US011830598B2

(12) United States Patent
Friedmann et al.

(10) Patent No.: US 11,830,598 B2
(45) Date of Patent: Nov. 28, 2023

(54) TEST AND OPTIMIZATION OF MEDICAL TREATMENTS FOR THE HUMAN EYE

(71) Applicant: UNIVERSITÄT HEIDELBERG, Heidelberg (DE)

(72) Inventors: Elfriede Friedmann, Gaiberg (DE); Simon Dörsam, Heidelberg (DE); Vladislav Olkhovskiy, Heidelberg (DE)

(73) Assignee: UNIVERSITÄT HEIDELBERG, Heidelberg (DE)

( * ) Notice: Subject to any disclaimer, the term of this patent is extended or adjusted under 35 U.S.C. 154(b) by 151 days.

(21) Appl. No.: 17/046,505

(22) PCT Filed: Apr. 2, 2019

(86) PCT No.: PCT/EP2019/058269
§ 371 (c)(1),
(2) Date: Oct. 9, 2020

(87) PCT Pub. No.: WO2019/197216
PCT Pub. Date: Oct. 17, 2019

(65) Prior Publication Data
US 2021/0110906 A1 Apr. 15, 2021

(30) Foreign Application Priority Data

Apr. 12, 2018 (EP) .................................... 18000349

(51) Int. Cl.
*G16H 20/17* (2018.01)
*B33Y 80/00* (2015.01)
(Continued)

(52) U.S. Cl.
CPC .............. *G16H 20/17* (2018.01); *B33Y 80/00* (2014.12); *G09B 23/285* (2013.01); *G16H 50/50* (2018.01)

(58) Field of Classification Search
CPC ........ G16H 20/17; G16H 50/50; B33Y 80/00; G09B 23/28; G09B 23/285
See application file for complete search history.

(56) References Cited

U.S. PATENT DOCUMENTS 9,437,119 B1 9/2016 Bernal
2008/0234322 A1* 9/2008 Syroid ................... A61K 31/02
514/731
(Continued)

OTHER PUBLICATIONS

Extended European Search Report Issued in European Application No. 18000349.3, dated Nov. 30, 2018.
(Continued)

*Primary Examiner* — Timothy A Musselman
(74) *Attorney, Agent, or Firm* — MEDLER FERRO WOODHOUSE & MILLS PLLC

(57) ABSTRACT

A computer-implemented method for testing ocular drug delivery is provided. The ocular drug delivery is characterized by a set of delivery parameters comprising at least one of drug type, drug concentration, drug amount, injection position, penetration depth. The method comprises: providing a model for the human eye, wherein the model comprises: a geometry equation defining a three-dimensional generalized limacon for the geometry of the vitreous body, geometry equations describing all components of the eye; and a set of equations defining a drug convection in the vitreous body; setting a target drug state in the vitreous body; using the model to perform at least one simulation of the ocular drug delivery with a given set of values for the set of delivery parameters, wherein the at least one simulation provides a simulated drug state in the vitreous body; comparing the target drug state and the simulated drug state.

19 Claims, 15 Drawing Sheets

(51) Int. Cl.
  *G16H 50/50*  (2018.01)
  *G09B 23/28*  (2006.01)

(56) References Cited

U.S. PATENT DOCUMENTS

2017/0165050 A1* 6/2017 Fripp ............... A61F 2/141
2018/0000339 A1  1/2018 Hipsley
2018/0153681 A1* 6/2018 Rosen .............. A61B 3/0025

OTHER PUBLICATIONS

International Search Report and Written Opinion in PCT/EP2019/058269, dated Aug. 5, 2019.
Communication Relating to the Results of the Partial International Search Report in PCT/EP2019/058269.
S. Dörsam et al., "Modeling and Simulations of Drug Distribution in the Human Vitreous", Topical Problems of Fluid Mechanics, DOI: https://doi.org/10.14311/TPFM.2017.013, Prague, Feb. 15-17, 2017, pp. 95-102.
N. Haghjou et al., "Computer Modeling of Drug Distribution after Intravitreal Administration", World Academy of Science, Engineering and Technology, International Journal of Medical, Health, Biomedical, Bioengineering and Pharmaceutical Engineering, vol. 5, No. 5, 2011, 11 pgs.
S. Friedrich et al., "Finite Element Modeling of Drug Distribution in the Vitreous Humor of the Rabbit Eye", Department of Chemical Engineering and Applied Chemistry, University of Toronto, Toronto, Ontario, Canada. Annals of Biomedical Engineering, vol. 25, 1997, pp. 303-314.
S. Friedrich et al.,"Drug Distribution in the Vitreous Humor of the Human Eye: The Effects of Aphakia and Changes in Retinal Permeability and Vitreous Diffusivity", Journal of Ocular Pharmacology and Therapeutics, Mary Ann Liebert Inc., vol. 13, Nov. 5, 1997, 15 pgs.
Yee Ling Yep et al., "3D printed bio-models for medical applications",Rapid Prototyping Journal, 2017,vol. 23, Issue: 2, pp. 227-235, https:/doi.org/10.1108/RPJ-08-2015-0102.
Ping Xie et al., "Application of 3-Dimensional Printing Technology to Construct and Eye Model for Fundus Viewing Study", PLOS/One, www.plosone.org, vol. 9, Issue 11, Nov. 2014, e109373, pp. 1-9.

* cited by examiner

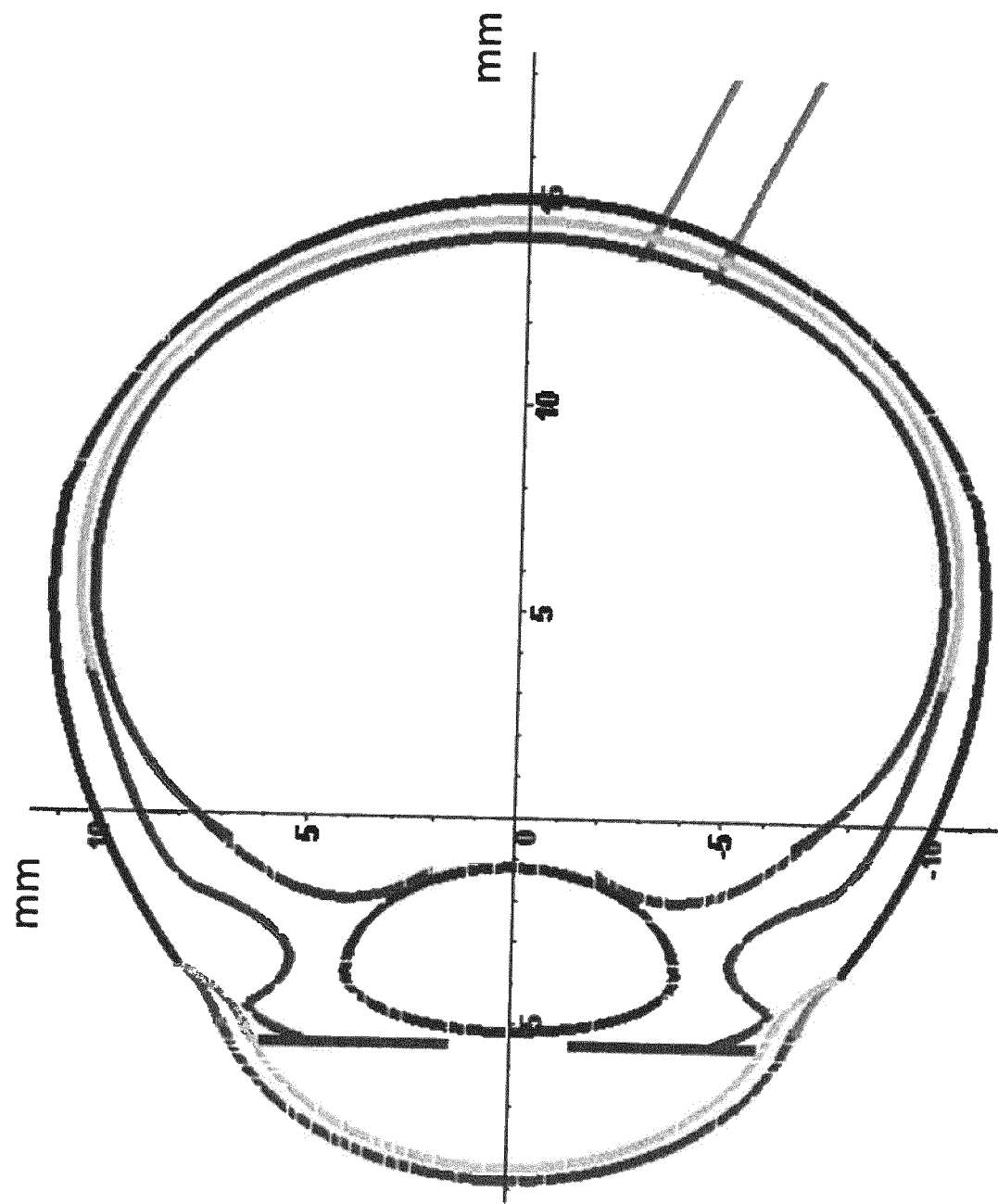

TEST AND OPTIMIZATION OF MEDICAL TREATMENTS FOR THE HUMAN EYE

CROSS-REFERENCE TO RELATED APPLICATIONS

This application is a 371 National Phase application of International Patent Application No. PCT/EP2019/058269, filed Apr. 2, 2019, which claims priority to EP Patent Application No. 18000349.3, filed Apr. 12, 2018, the disclosures of which are incorporated by reference herein in their entirety.

TECHNICAL FIELD

The following description relates to a computer-implemented method, a computer program product and a computer system for testing and optimizing medical treatments of the human eye.

BACKGROUND

The human eye comprises a plurality of components, including the vitreous body, the lens, the ciliary body, the iris, the anterior chamber and the cornea. The individual components have different shapes and different properties, such as mechanical properties (e.g. consistency) and optical properties. Further, the characteristics of a given component may be affected by pathologies of the eye, such as glaucoma and retinal diseases, or conditions such as myopia.

In order to treat the pathologies/conditions, the properties of the components, which determine at least partly the physiological processes occurring in the human eye, need to be understood. For example, the vitreous body acts as a mechanical damper and transmits stresses protecting the eye. However, although linked to several pathologies such as retinal detachment, the structure of the vitreous body is not well understood.

Further, there is a problem with testing different therapeutic approaches for treating the pathologies/conditions, because in vitro or in vivo tests suffer from limitations in the tests that can be performed due to availability, costs and ethical considerations.

Therefore, there is a need for an accurate understanding of the structure of the eye based on which tests of different therapeutic approaches can be correctly and efficiently performed.

SUMMARY

It is an object of the invention to allow for accurate and efficient testing of medical treatments for the eye.

The achievement of this object in accordance with the invention is set out in the independent claims. Further developments of the invention are the subject matter of the dependent claims.

According to one aspect, a computer-implemented method for testing ocular drug delivery is provided, wherein the ocular drug delivery is characterized by a set of delivery parameters comprising at least one of drug type, drug concentration, drug amount, injection position, penetration depth. Administration of drugs is one of the possible medical treatments for eye pathologies. Exemplarily, the drug may be parenterally administered by means of ocular deliver via intravitreal injection. In this case, a needle punctures the external surface of the vitreous body and penetrates the vitreous body up to a given penetration depth. The drug contained in e.g. a syringe coupled to the needle is then released inside the vitreous body.

Exemplary diseases that are treated by means of intravitreal injection include but are not limited to retinal diseases such as age-related macular degeneration (AMD), diabetic retinopathy and retinal vein occlusions. Exemplary drugs used to treat such diseases include but are not limited to anti-vascular endothelial growth factor (anti-VEGF) substances (e.g. Aflibercept) and steroid medications.

The ocular drug delivery may be performed in practice in a plurality of different manners. In particular, the ocular drug delivery may be considered as determined by a set of delivery parameters characterizing the specific ocular drug delivery. In other words, the above generally-defined process of intravitreal injection is concretized by specific values for the set of delivery parameters (also called delivery variables). In particular, the set of delivery parameters may comprise one or more delivery parameters. Each delivery parameter may assume a plurality of values, wherein the values may be numerical values, e.g. confined to a given numerical range, or non-numerical values, such as specifications of non-quantifiable features of the delivery.

For example, the ocular drug delivery may be performed using different types of drugs, hence the ocular drug delivery is characterized by which drug is being administered to a patient. The drug type may be a delivery parameter which takes non-numerical values, since it is a qualitative indication. The drug type may indicate a family of drugs having substantially similar behaviors when injected in the vitreous body or identify the specific drug. Indeed, different drugs may behave differently in terms of convection within the vitreous body.

Another delivery parameter characterizing the drug may be the drug concentration, i.e. the abundance of the actual medicament divided by the total volume of the mixture administered to the patient. Indeed, in some cases, the drug may be provided in a diluted form. The drug concentration may assume a numerical value, expressed e.g. as a percentage value.

Yet another delivery parameter concerning the drug may be the drug amount, i.e. the quantity of drug being administered to the patient. The drug amount may take a numerical value, expressed as a real number in mL or cc.

Additional delivery parameters may describe the needle injection rather than the drug being injected. One such delivery parameter may be the injection position, i.e. the position at which the needle enters the eye. The injection position may also comprise an injection direction. The needle may enter at a given point and have any inclination in the solid angle subtended by the injection point. The injection position, including the injection direction, may be specified by numerical values providing coordinates for a point in space and two values for angles defining a direction in the solid angle. The point in space may also be expressed with reference to the eye anatomy. The coordinate system with respect to which coordinates are provided may be a fixed coordinate system relative to the human eye.

Another such delivery parameter may be the penetration depth of the needle, i.e. the extent to which the needle is within the vitreous body or, in other words, the length of the part of the needle inside the vitreous body. The penetration depth may be specified by a numerical value e.g. a real number in mm.

Further delivery parameters may include presence and type of additional substances that may act in combination with the drug once delivered inside the vitreous body, dimensions and type of needle, timing of administration (e.g. the drug is delivered all at once or in time-spaced intervals).

The method for testing ocular drug delivery comprises providing a model for the human eye, wherein the model comprises: a geometry equation defining a three-dimensional limacon for the geometry of the vitreous body; and a set of equations defining a drug convection (diffusion and advection) in the vitreous body.

The model for the human eye is a conceptual description that mirrors the actual human eye in that it is capable of reproducing intrinsic features of the human eye, such as its shape, as well as interactions with and/or reactions to external elements, such as light or drugs. The model may particularly be a mathematical model that describes the human eye by means of equations.

The model may comprise in particular a geometry equation for describing the shape of the vitreous body, more specifically of the outer surface thereof. Exemplarily, the vitreous body may be described as a three-dimensional limacon, which is an extension of the canonically defined limacon, which has two dimensions. The three-dimensional limacon is defined by the following equation in parametric form in spherical coordinates:

$$x = R(\varphi)\cos\varphi + m_x$$

$$y = R(\varphi)\sin\varphi \cos\theta$$

$$z = R(\varphi)\sin\varphi \sin\theta$$

wherein $\theta \in [0, \pi)$, $\varphi \in [0, 2\pi)$. Generally, $R(\varphi)$ may include trigonometric functions of $\varphi$ and one or more parameters that define the specific shape of the limacon, denoted, together with $m_x$, as "geometry parameters" hereinafter. In one particular example, the three-dimensional limacon may be defined by the equations above, wherein $$R(\varphi) = p_1 + \sum_{i=2}^{n} p_i \cos\varphi^{2i-3},$$

with n a natural number. Accordingly, the three-dimensional limacon is not just an extension of a standard limacon to three dimensions, but it is further generalized in order to realistically describe the shape of the vitreous body. For example, n may be chosen to be equal to 3, so that $$R(\varphi) = (p_1 + p_2 \cos\varphi + p_3 \cos\varphi^3),$$

with $m_x$, $p_1$, $p_2$ and $p_3$ as geometry parameters. Exemplarily, the values for the geometry parameters may belong to the following ranges:

$$p_1 \in [7.5, 7.7], p_2 \in [9.0, 9.2], p_3 \in [-2.5, -2.8], m_x \in [-1, -1.2].$$

In other examples, n may have a different value or $R(\varphi)$ may have a different form.

When providing the model, the values for the geometry parameters may be already fixed. Accordingly, in one particular implementation, each geometry parameter may have a predetermined, constant value that is part of the model. The values for the geometry parameters may have been determined on the basis of experimental and/or literature data about the shape of the vitreous body.

In another particular implementation, the method may further comprise determining the value(s) for the geometry parameter(s). In other words, the geometry equation may be considered as a parameterized geometry equation including a set of free geometry parameters, and the method may further comprise: retrieving eye measurement data describing at least the shape of the vitreous body; and determining a set of values for the set of free geometry parameters by fitting the parameterized geometry equation to the eye measurement data.

The set of geometry parameters may comprise one or more geometry parameters. The geometry parameters may be "free" in the sense that they do not have a fixed, predetermined value that is part of the model, but are initially undetermined. Only after a fitting operation are the values of the geometry parameters specified.

The eye measurement data may comprise at least data describing the shape of the vitreous body. Such data may be obtained by measuring the shape of the vitreous body in actual human eyes with an imaging technique, e.g. ultrasound, magnetic resonance imaging or optical coherence tomography. The eye measurement data may exemplarily be represented by a plurality of points in a three-dimensional space, so that the data may include a list of three-dimensional coordinates as measured for different points on the surface of the vitreous body. The eye measurement data may relate to a single human eye or to a plurality of human eyes.

In one exemplary implementation, retrieving the eye measurement data comprises collecting the eye measurement data, i.e. performing the measurements on one or more human eyes using an imaging technique. In addition to the collected data, eye measurement data coming from measurements performed in the past or from the literature may be used. In another exemplary implementation, retrieving the eye measurement data only consists of retrieving data obtained from previous measurements or from the literature, without actively collecting the eye measurement data. In both cases, the data may be retrieved from a storage medium into which collected data are stored together with past collected data and/or literature data, which may be a local storage medium or a remote storage medium. For example, the data may be stored in a database.

In addition to describing the shape of the vitreous body, the eye measurement data may describe additional features of the vitreous body, such as its consistency in terms e.g. of viscosity and permeability, which may be obtained using appropriate techniques. Further, the eye measurement data may describe other components of the eye, e.g. the iris or the anterior chamber. In some examples, the eye measurement data may describe the structure of the whole human eye.

On the basis of the eye measurement data, a fit may be performed to determine a set of values for the set of free geometry parameters. If the eye measurement data relate to a plurality of human eyes, the set of values for the set of geometry parameters may be determined by fitting all data. In this case, a geometry equation for an "average" human eye may be obtained. Instead, if the eye measurement data refer to a single eye, an individualized modelling of an eye of an individual may be achieved.

It should be noted that, both in the case in which the values for the geometry parameters are fitted on the fly and in the case in which the values are predetermined, the geometry equation may describe the eye of an individual or the "average" human eye. Indeed, in any way the predetermination of the values is preferably based on eye measurement data. A specific difference between the two exemplary implementations is that in one case the values are actively determined by fitting and in the other case they are stored, fixed values obtained from previously performed fittings. In other words, the two exemplary implementations are not necessarily mutually exclusive: the set of values may be obtained by fitting the eye measurement data and then used as default set of values in all subsequent executions of the method. In other examples, however, the set of values may be determined every time anew, e.g. based on different eye measurement data, such as individual data.

The geometry equation may have different values for the geometry parameters according to whether the vitreous body is healthy or pathologic. For example, with age the consistency of the vitreous body changes, namely it liquefies, so that a collapse of the vitreous body and a detachment of the posterior surface may be observed. Accordingly, the outer surface of the vitreous body may exemplarily show some "dents", so that the geometry parameters may vary, albeit slightly, between a healthy eye and a pathological one. Exemplarily, the geometry equation for a pathological vitreous body may be split into two equations with different parameters, one describing the relatively healthy part and the other one describing the liquefied part. Geometry parameters for a pathological vitreous body may be obtained from data measured from one or more individuals affected by the pathology.

Further to the geometry equation, the model may comprise a set of equations defining a drug convection in the vitreous body, namely the way the drug molecules are transported within the vitreous body after being ejected from the needle. The vitreous body is made of the vitreous humor, which is an incompressible, transparent fluid made up of water (98%), collagen, hyaluronic acid and proteins. Accordingly, the convection of the drug may be at least partly determined by how the vitreous humor flows within the vitreous body, since the drug moves with the vitreous humor. Specifically, the convection of the drug may take place both via advection (i.e. with bulk flow) and diffusion (i.e. without bulk flow). Thus, the set of equations may comprise the advection-diffusion equation $$\partial_t C(t,\vec{x}) + [\vec{v}(t,\vec{x}) \cdot \nabla] C(t,\vec{x}) - \nabla \cdot [D(\vec{x}) \nabla C(t,\vec{x})] = f_g$$

wherein $C(t,\vec{x})$ is the concentration of the drug, $\vec{v}(t,\vec{x})$ is the velocity of the vitreous humor, $D(\vec{x})$ is the diffusion coefficient and $f_g$ is the effect of the gravitational force on the drug concentration $C(t,\vec{x})$. The concentration of the drug $C(t,\vec{x})$ is not to be confused with the concentration as delivery parameter and $C(t,\vec{x})$ may be also denoted as concentration function. The concentration function indicates the amount of drug per unit volume of vitreous humor. The effect of the gravitational force $f_g$ may be calculated as follows:

$$f_g = \frac{g}{\beta}\left(1 - \frac{\rho_0}{\rho}\right)\partial_x C(t,\vec{x}),$$

wherein $\rho_0 = 1.0071 \cdot 10^3$ kg/m³ is the density of the vitreous body, $\rho = 1.37 \cdot 10^3$ kg/m³ is an exemplary density of the drug, g is the gravitational acceleration and $$\beta = \frac{6\pi r v}{m},$$

with v the viscosity of the vitreous humor, equal to $6.9 \cdot 10^{-4}$ kg/(m·s), and $m = 1.9 \cdot 10^{-22}$ kg and $r = 3.7 \cdot 10^{-9}$ m are the mass and the radius of a drug particle, respectively. The partial derivative is made with respect to the direction in which the gravity act, e.g. the x axis if the patient is lying or the z axis if the patient is in the upright position.

The diffusion coefficient depends on the direction in order to account for an anisotropic diffusion. Indeed, in a healthy vitreous body, the collagen fibers create a meshwork with a heterogeneous structure that determines an anisotropic diffusion. A pathological vitreous body, e.g. an aged one, tends to liquefy. Exemplarily, the diffusion coefficient may be described by a 3×3 matrix given by:

$$D := d_1 I + d_2 (f \otimes f), f = (\cos\theta, \sin\theta, 0)^T$$

wherein $d_1$ is a parameter describing the proportion of isotropic diffusion and $d_2$ is a parameter describing the proportion of directed diffusion along the collagen fibers. The values for the parameters $d_1$ and $d_2$ may be real numbers in the range [0,1]. The values for the parameters $d_1$ and $d_2$ may be determined on the basis of theoretical considerations and/or experiments. It should be noted that the values for $d_1$ and $d_2$ may differ in a healthy eye and in a pathological one, since the consistency may vary as explained above.

Since the vitreous humor is an incompressible fluid, the velocity $\vec{v}(t,\vec{x})$ is a solenoidal vector field, namely the following divergence equation applies:

$$\nabla \cdot \vec{v}(t,\vec{x}) = 0,$$

which may be another equation in the set of equations defining the drug convection.

Further, the set of equations may comprise a third equation for the description of the vitreous humor flow that takes into account the fact that the collagen meshwork makes the vitreous body a porous medium, the so-called Darcy equation:

$$\frac{v}{K}\vec{v}(t,\vec{x}) + \nabla p(t,\vec{x}) = h_g$$

wherein $p(t,\vec{x})$ is the pressure of the vitreous humor flow, $h_g$ is the effect of the gravitational force on the vitreous humor flow, v is the viscosity and K is the hydraulic conductivity of the vitreous body. The values for v and K may be determined on the basis of theoretical considerations and/or experiments and may differ in a healthy eye and in a pathological one. The relative value of the hydraulic conductivity to the viscosity is $K/v = 8.4 \times 10^{-11}$ m²/(Pa·s). The effect of the gravitational force is calculated as $h_g = \rho g$.

Accordingly, in one example, the set of equations may be a system of equations comprising the advection-diffusion equation, the divergence equation and the Darcy equation. The values for the parameters in these equations, such as K or $d_1$, may be provided as fixed parts of the model, may be retrieved from a storage medium or may be input by a user.

Further, the set of equations may comprise one or more boundary conditions for the quantities involved in the system of equations discussed above. The boundary conditions may be given by theoretical constrains based on the eye physiology and/or by measurements derived from experiments. In particular, the boundary conditions may be defined with respect to the surface of the vitreous body as described by the geometry equation. Exemplarily, different areas of the surface of the vitreous body may present different boundary conditions, so that the surface may be divided in regions, such as the region of the vitreous body confining with the lens, the region confining with the retina and the region confining with the ciliary body.

Based on the point in time during the convection process, the drug may be in a given state in the vitreous body, namely the drug may be present in the vitreous body in a given amount and with a given spatial distribution. In other words, the drug may be found at various locations in the vitreous body, possibly with different concentrations at the different locations. Accordingly, the drug state may be defined by the concentration function $C(t,\vec{x})$. The state may vary with time based on the convection process, and the drug may eventually no longer be found in the vitreous body, because it has been absorbed by the human body. The drug state may be influenced by one or more of the delivery parameters. For example, the injection point may affect how the drug is distributed in the vitreous body.

In order for the ocular drug delivery to be effective in treating a pathology, a particular state of the drug may have to be achieved at a given point in time. For example, a persistence of the drug in the vitreous body for a predetermined amount of time may be required and/or the presence of the drug in a particular region of the vitreous body may be necessary.

Accordingly, the method comprises setting a target drug state in the vitreous body. The target drug state is a desired state of the drug on the grounds that this particular state makes the ocular drug delivery effective for the treatment purposes.

The drug state may be characterized by one or more performance factors derived from the concentration function, such as the total amount of drug present in the vitreous body at a given time, the amount of drug in a given region of the vitreous body at a given time, the point in time at which the drug concentration in the vitreous body becomes negligible (i.e. lower than a predetermined threshold), the rate of change of the drug concentration versus time, and others.

The performance factors are measurable quantities derived from $C(t,\vec{x})$ that provide an indication on the effectiveness of the treatment. Exemplarily, the definition of the performance factors may involve the computation of volumes inside the vitreous body, and, thus, the geometry equation may be used.

In one example, the target drug state may be set by defining constraints on the concentration function directly, e.g. a target value for a given time t and given location $\vec{x}$. In another example, the target drug state may be set via the one or more performance factors.

Specifically, constraints may be set on the one or more performance factors, such as boundaries for the numerical values of the performance factors or exact values. In other words, the constraints may be in the form of numerical values. If more than one performance factor is used for setting the target drug state, it may be sufficient that only the conditions on one performance factor or a proper subset of the used performance factors be met, or the conditions set for all factors may have to be met.

The target drug state may be set on the basis of theoretical and/or experimental considerations. In particular, the conditions for the one or more performance factors may be derived from physical principles and/or from previously performed tests (real or simulated) about the drug delivery. These conditions may be taken from the literature, which may make use of theory and/or experiments, and/or be inferred from experiments directly performed.

In some examples, the constraints on the one or more performance factors, e.g. a set of numerical values, may be stored in a storage medium and retrieved therefrom. In other examples, the constraints may be input by a user by means of a user interface and an input device, such as a keyboard.

Exemplarily, the target drug state may be characterized by the following performance factors:

$$J_1(t) := \frac{\int_\Omega C(t,\vec{x})dx}{\int_\Omega C(0,\vec{x})dx}$$

i.e. the relative amount of drug left in the whole volume $\Omega$ of vitreous body at a given time with respect to the initial amount, and $$J_2(t):=\int_{B_r} C(t,\vec{x})dx$$

i.e. the amount of drug in a specific region $B_r$, such as a region around the macula. For example, a target drug state may be defined by the conditions $J_1(\bar{t}) \geq T_1$ and/or $J_2(\bar{t}) \geq T_2$ for a given point in time $\bar{t}$, with $T_1$ and $T_2$ predetermined thresholds.

In order to test the ocular drug delivery prior to actually performing the ocular drug delivery on a patient, the method comprises using the model to perform at least one simulation of the ocular drug delivery with a given set of values for the set of delivery parameters, wherein the at least one simulation provides a simulated drug state in the vitreous body.

The simulation of the ocular drug delivery is an imitation of the execution of the ocular drug delivery in the real world performed by means of a computer system. The set of equations defining the drug convection models the evolution of the process with time, while the set of values for the set of delivery parameters provides initial conditions for the simulation. In particular, the geometry equation, as explained above, may be used for providing boundary conditions in the set of equations. In particular, the finite element method may be used for numerically solving the model equations.

The delivery parameters may be considered to be the simulation parameters. Indeed, if the simulation uses the same given model for the convection of the drug in the vitreous body, the degrees of freedom in the simulation are given by the values for the simulation parameters. In other words, the result of the simulation is affected by the values for the simulation parameters.

As explained above, the convection process determines a state of the drug in the vitreous body. Thus, one result of the simulation may be a simulated drug state. In particular, the simulation may provide values for the function $C(t,\vec{x})$ within the vitreous body at different times and different points. Specifically, the result of the simulation may be a discrete set of values $c(t_i,\vec{x}_j)$ for a discrete set of time points $t_i$, with $i=1,\ldots,N$, and a discrete set of spatial points $\vec{x}_j$ with $j=1,\ldots,M$, N and M being natural numbers dependent on the resolution of the simulation. Performance factors may be derived from the simulated concentration function, as discussed above.

The simulated drug state is then compared to the target drug state in order to assess how effective an ocular drug delivery performed in a manner defined by the set of delivery parameters is. If the simulated drug state is sufficiently similar to the target drug state, it may be inferred that the specific ocular drug delivery is suitable for treating the pathology in question. If the simulated drug state substantially deviates from the target drug state, the specific ocular drug delivery may not be considered acceptable for the treatment purpose.

The simulated drug state and the target drug state may be compared by directly comparing the concentration function. The use of performance factors may make the comparison easier, because two single values may be compared to each other. Accordingly, in a particular implementation, the method may further comprise defining a performance factor characterizing a drug state and setting the target drug state may comprise setting a target constraint for the performance factor; providing a simulated drug state may comprise computing a simulated value for the performance factor; comparing the target drug state and the simulated drug state may comprise comparing the simulated value with the target constraint. The same applies for a plurality of performance factors characterizing the drug state.

The compliance of the simulated value with the target constraint may be determined on the basis of a given threshold. If the simulated value meets the target constraint within a certain tolerance, the test may be positive, in that the ocular drug delivery may result suitable for effective treatment.

In particular, if the target constraint is an exact value for the performance factor, if the difference or relative difference between the exact value and the simulated value is lower or equal to a given threshold, the target may be considered met. For example, the threshold for the relative difference may be 0.05, or 0.02, or 0.01. In certain cases, no tolerance may be allowed, so that the difference has to be 0. If the target constraint is a range, which may have a lower bound and/or an upper bound, the target may be considered met if the simulated value is within the range or if it deviates from the lower/upper bound up to a given threshold. In other examples, the simulated value may have to be strictly within the range of the target constraint.

Therefore, based on how the result of the simulation compares to a given target, a user may obtain information on the performance of a specific ocular drug delivery, i.e. an ocular drug delivery performed with a given set of delivery parameters.

In a particular implementation, the computer system may be used to select an optimal set of values for the set of delivery parameters. Accordingly, the model may be used to perform a plurality of simulations of the ocular drug delivery, each simulation being performed with a different set of values for the set of delivery parameters and each simulation providing a simulated drug state in the vitreous body. The method may further comprise: computing a plurality of deviation scores for the plurality of simulations based on the comparison between the target drug state and the plurality of simulated drug states; selecting an optimal set of values for the set of delivery parameters based on the deviation scores.

Different sets of values for the set of delivery parameters may differ by the value of one delivery parameter or the values of more delivery parameters.

The resulting simulated drug state may be different for each simulation because of the different sets of values used for the set of delivery parameters, however in some cases a delivery parameter may turn out to have a negligible impact on the simulated drug state or the modification of more delivery parameters may "balance out".

Each resulting simulated drug state is compared with the target drug state, in any of the manner described above for a single simulation. In particular, a deviation score may be computed for each simulation according to a deviation between the simulated drug state and the target drug state. The deviation score may be a numerical value indicating the degree of compliance of the simulation result with the set target.

If the comparison is performed directly on the basis of the concentration function, i.e. comparing the target $C(t,\vec{x})$ with the simulated $C(t,\vec{x})$, the absolute difference between the two functions may be computed e.g. for each time point and spatial point of the discrete set resulting from the simulation. The deviation score may be the mean or the median of all differences.

If the comparison is performed between performance factor values, the absolute difference between the target value and the simulated value may be computed as deviation score. If the target constraint is not a single value but a range, the difference with the central value of the range or the upper bound or the lower bound may exemplarily be used for computing the difference. If more performance factors are considered, the deviation score may be a possibly weighted mean of the differences for each performance factor. Other examples for computing the deviation score are within the capabilities of the skilled person.

It should be noted that according to how the target drug state is set and how the deviation score is computed, the deviation score may be low or high when indicating a good match with the target. In the case of an exact target value, the lower the deviation score, the closer the simulated drug state is to the target drug state. If the target drug state is defined by a range with only a lower limit, and the deviation score is computed as difference between the lower limit and the simulated value, a simulated value within the range and far apart from the lower limit, i.e. with a high deviation score, is better than one with a lower deviation score.

In one example, the deviation scores computed for the plurality of simulations may be compared among each other to identify the best deviation score, i.e. the deviation score that indicates better match with the target. Accordingly, the set of values for the set of delivery parameters corresponding to the best deviation score may be selected as the optimal. It should be noted that such a selection only indicates a relative suitability of one particular set of values with respect to other sets and does not necessarily imply an optimal effectiveness of the ocular drug delivery. In other words, the selection is only made among the simulations that were actually run.

In another example, the computer system may be used to automatically optimize the delivery parameters in view of the target, exploring the parameter space to find the best solution. The deviation score computed as explained above yields a number whose value is dependent, among others, on the values assigned to the delivery parameters. Thus, the deviation score may be seen as a function of the one or more delivery parameters, hereafter called "deviation function". The deviation function may be numerically identified by the computer system from the plurality of computed deviation scores.

The deviation function may be optimized to find the best values for the delivery parameters, i.e. those values for which the ocular drug delivery is most effective. Finding the optimal values for the delivery parameters is an optimization problem in which the deviation function is minimized or maximized by systematically choosing input values and computing the value of the deviation function. The input values may be chosen among the plurality of sets of values used for the simulations and/or in mathematical neighborhoods thereof. Depending on the number of delivery parameters, the optimization problem may be a multi-dimensional problem: For the optimization, only numerical delivery parameters may be considered. Examples of optimization algorithms are the Nelder-Mead method and the steepest descent method.

The result of optimizing is that the parameter value or the combination of parameter values that give the best deviation score is found. In addition or alternatively to finding the optimal values for the delivery parameters, acceptable ranges may be found by constraining the deviation function to assume a value (i.e. the deviation score) below a specific predetermined threshold. There may be more than one acceptable range for a given delivery parameter. The threshold may be input by a user or may be fixed to a given value such as 0.01 or 0.05. In particular, the term "range" should be construed broadly to encompass multi-dimensional results. Accordingly, the result of the target determination step may be a single point in the delivery parameter space and/or a curve or surface in the delivery parameter space.

In a particular implementation, the method may further comprising generating a visual representation of the simulated drug state in the vitreous body; and outputting the visual representation via an output device.

For example, a three-dimensional plot may be generated for $C(t,\vec{x})$, wherein the plot for the concentration function may be visualized within a plot of the three-dimensional limacon representing the vitreous body. The output device may be e.g. a screen.

In some examples, also a plot of the target drug state may be generated, in order to provide a visual comparison.

In a further particular implementation, the method may further comprise three-dimensionally printing the vitreous body using the geometry equation. Further, the model for the human eye may comprise a plurality of geometry equations, each describing mathematically the shape of one eye component. Exemplarily, the eye components that may be described by the plurality of geometry equations may include: natural lens, artificial lens, iris (healthy or pathological), ciliary body, sclera, cornea and anterior chamber. The plurality of equations may have the forms described below. On the basis of the plurality of equations, a complete artificial human eye may be printed with a three-dimensional printer.

A three-dimensional print of the human eye may enable further tests of medical treatments. For example, in the three-dimensional print of the human eye, particle image velocimetry (PIV) measurements may be performed.

In another aspect of the invention, a computer program product is provided. The computer program product comprises computer-readable instructions, which, when loaded and executed on a computer system, cause the computer system to perform operations according to the method described above.

In yet another aspect of the invention, a computer system for testing ocular drug delivery is provided, wherein the ocular drug delivery is characterized by a set of delivery parameters comprising at least one of drug type, drug concentration, drug amount, injection position, penetration depth. The system comprises:
means for providing a model for the human eye, wherein the model comprises:
a geometry equation defining a three-dimensional limacon for the geometry of the vitreous body; and
a set of equations defining a drug convection in the vitreous body;
means for setting a target drug state in the vitreous body; means for using the model to perform at least one simulation of the ocular drug delivery with a given set of values for the set of delivery parameters, wherein the at least one simulation provides a simulated drug state in the vitreous body; means for comparing the target drug state and the simulated drug state.

Exemplarily, the means for providing the model and for setting a target drug state may include a storage unit in which the model and the target drug state are stored, and/or may include an input unit such as a keyboard or a mouse and/or may include a communication unit configured to retrieve the model and the target drug state from a remote storage. Further, a processing and control unit may be part of one or more means of the system and may be configured to run the simulation, compare the target drug state and the simulated drug state and generally to control the operations of the other units.

To summarize, the invention as described above is used to test different therapeutic approaches by means of simulations, so that virtual experiments can be carried out numerous times and various hypotheses can be easily and accurately tested prior to being employed on a patient. Accordingly, development of new medical treatments for eye pathologies is facilitated. Indeed, the use of the simulation allows a pre-selection of promising therapies. Further, existing medical treatments may be optimized, generally or for a specific individual. Medical treatments may include, besides administration of medicaments like drugs, products like lenses and microstents or surgery.

BRIEF DESCRIPTION OF THE DRAWINGS

Details of exemplary embodiments are set forth below with reference to the exemplary drawings. Other features will be apparent from the description, the drawings, and from the claims. It should be understood, however, that even though embodiments are separately described, single features of different embodiments may be combined to further embodiments.

FIG. 13 shows a geometric model for the eye as a whole.

DETAILED DESCRIPTION

In the following, a detailed description of examples will be given with reference to the drawings. It should be understood that various modifications to the examples may be made. Unless explicitly indicated otherwise, elements of one example may be combined and used in other examples to form new examples.

Figure 1:
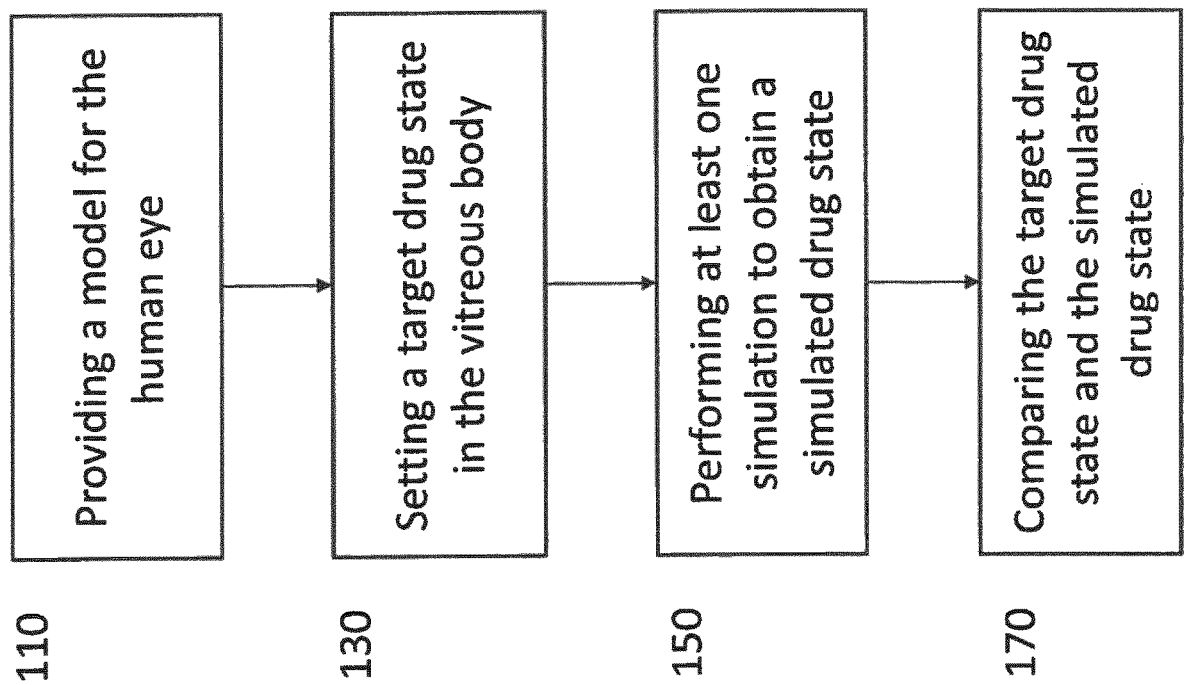
FIG. 1 shows an exemplary method for testing an ocular drug delivery.

FIG. 1 shows an exemplary method for testing an ocular drug delivery. The ocular drug delivery may be characterized by one or more delivery parameters. In this particular example, the set of delivery parameters comprises one element, namely the injection position. The injection position is the location at which the needle is inserted into the eye and the orientation at which the needle is inserted. Accordingly, in this case, the method may in particular test the efficacy of the drug administration with respect to the injection position.

Figure 2B:
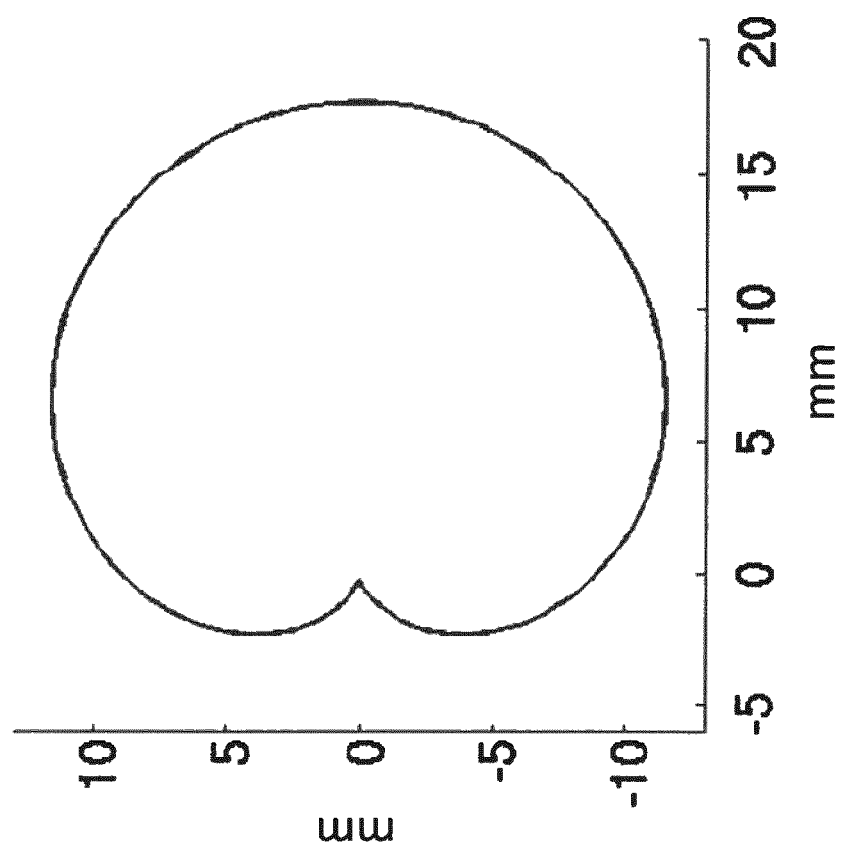
FIGS. 2a to 2d show the shape of the vitreous body from different perspectives.
Figure 2A:
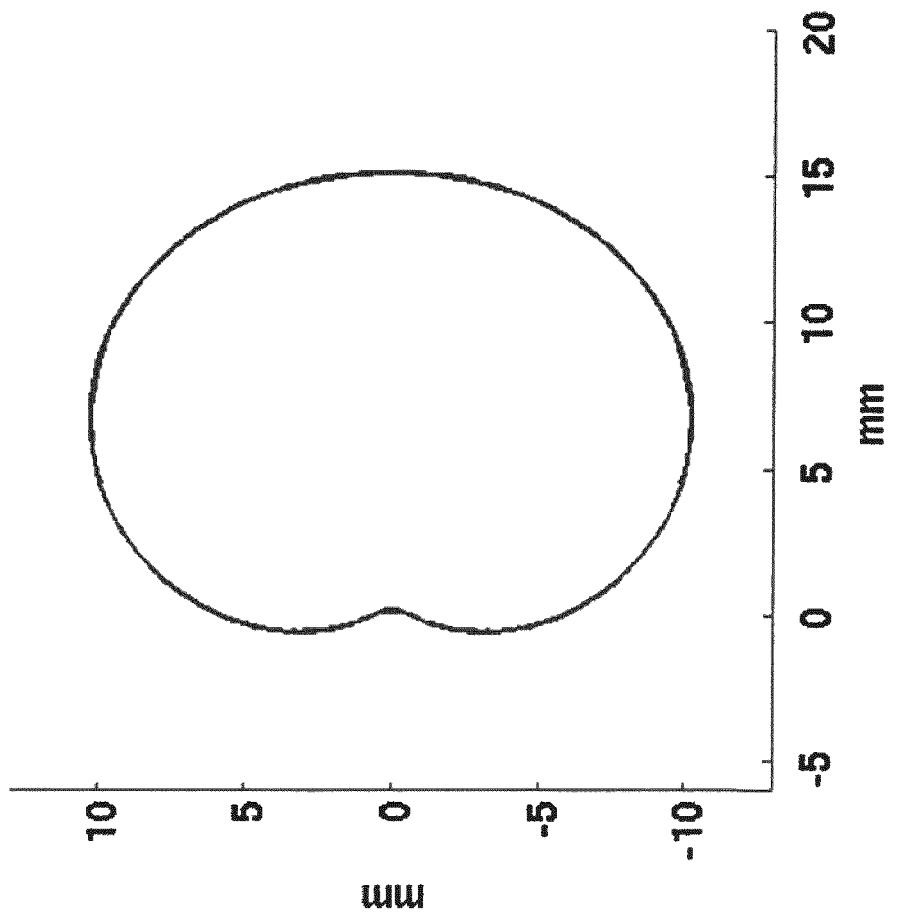

The method comprises providing a model for the human eye at step 110. The model is a mathematical model including a geometry equation defining a three-dimensional limacon for the geometry of the vitreous body. The geometry equation is:

$$x = R(\varphi)\cos\varphi + m_x$$

$$y = R(\varphi)\sin\varphi \cos\theta$$

$$z = R(\varphi)\sin\varphi \sin\theta$$

with $R(\varphi) = (p_1 + p_2 \cos\varphi + p_3 \cos\varphi^3)$, wherein $\theta \in [0,\pi), \varphi \in [0, 2\pi)$. The parameters $p_1$, $p_2$ and $p_3$ define the exact shape of the limacon, while $m_x$ depends on the position of the origin of the coordinate system. The two-dimensional projection in the x-y plane of the three-dimensional surface defined by the geometry equation is shown in FIG. 2a. For comparison, FIG. 2b shows the canonical two-dimensional limacon. It can be seen that the geometry equation defines a generalized three-dimensional limacon, which has an additional parameter for defining the shape, $p_3$. In virtue thereof, a realistic representation of the vitreous body can be achieved.

Figure 2C:
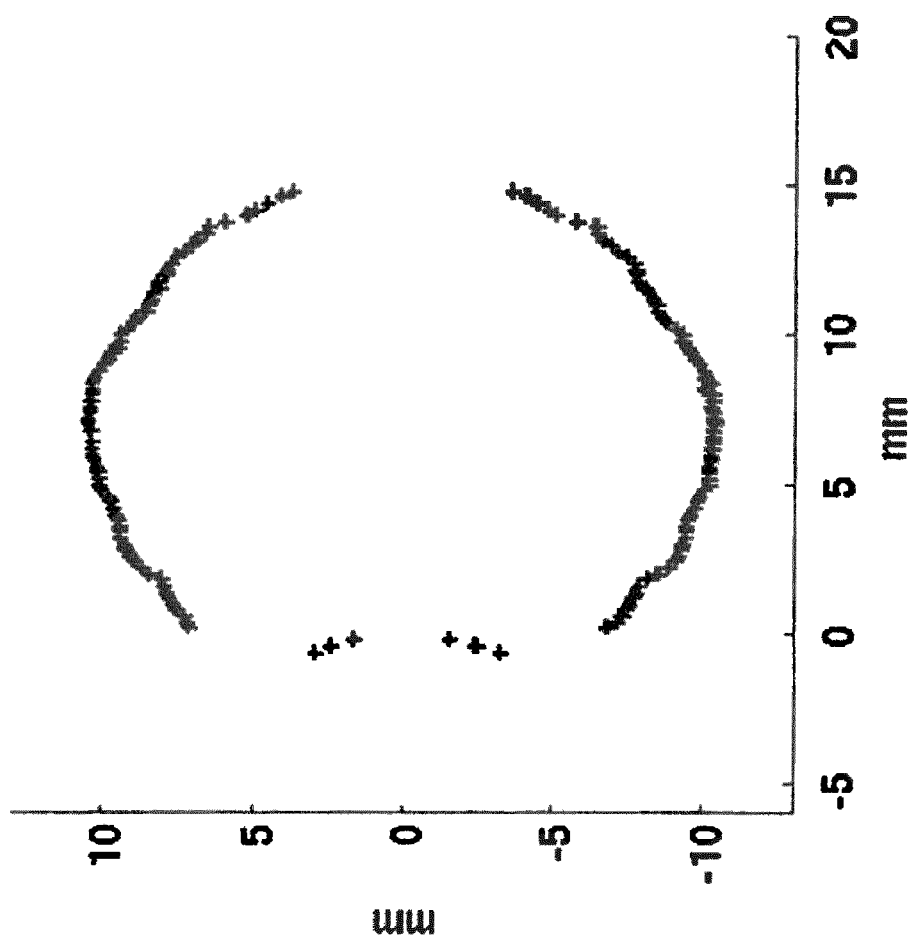

The values for the geometry parameters $p_1$, $p_2$, $p_3$ and $m_x$ are obtained by fitting eye measurement data as shown in FIG. 2c. The eye measurement data about the shape of the outer surface of the vitreous body are obtained by means of ultrasound imaging technique. The eye measurement data comprise a plurality of coordinates for points on the outer surface of the vitreous body. The data points shown in FIG. 2c are the two-dimensional projections of the eye measurement data.

By fitting a plurality of measurement data collected for a plurality of eyes, the formula for an average vitreous body can be determined. Exemplarily, the parameters describing an average vitreous body are: $p_1 = 7.59$ mm, $p_2 = 9.13$ mm, $p_3 = -2.66$ mm and $m_x = -1.08$ mm.

In particular, the relation between $m_x$ and the coordinates $(r_i, \phi_i)$ of a point of the outer surface of the vitreous body when projected in the x-y plane are:

$$\phi_i(m_x) = \arccos\left(\frac{x_i - m_x}{r_i}\right), \quad r_i = \sqrt{(x_i - m_x)^2 + y_i^2}.$$

The value for $m_x$ is determined from the above relation.

Figure 2D:
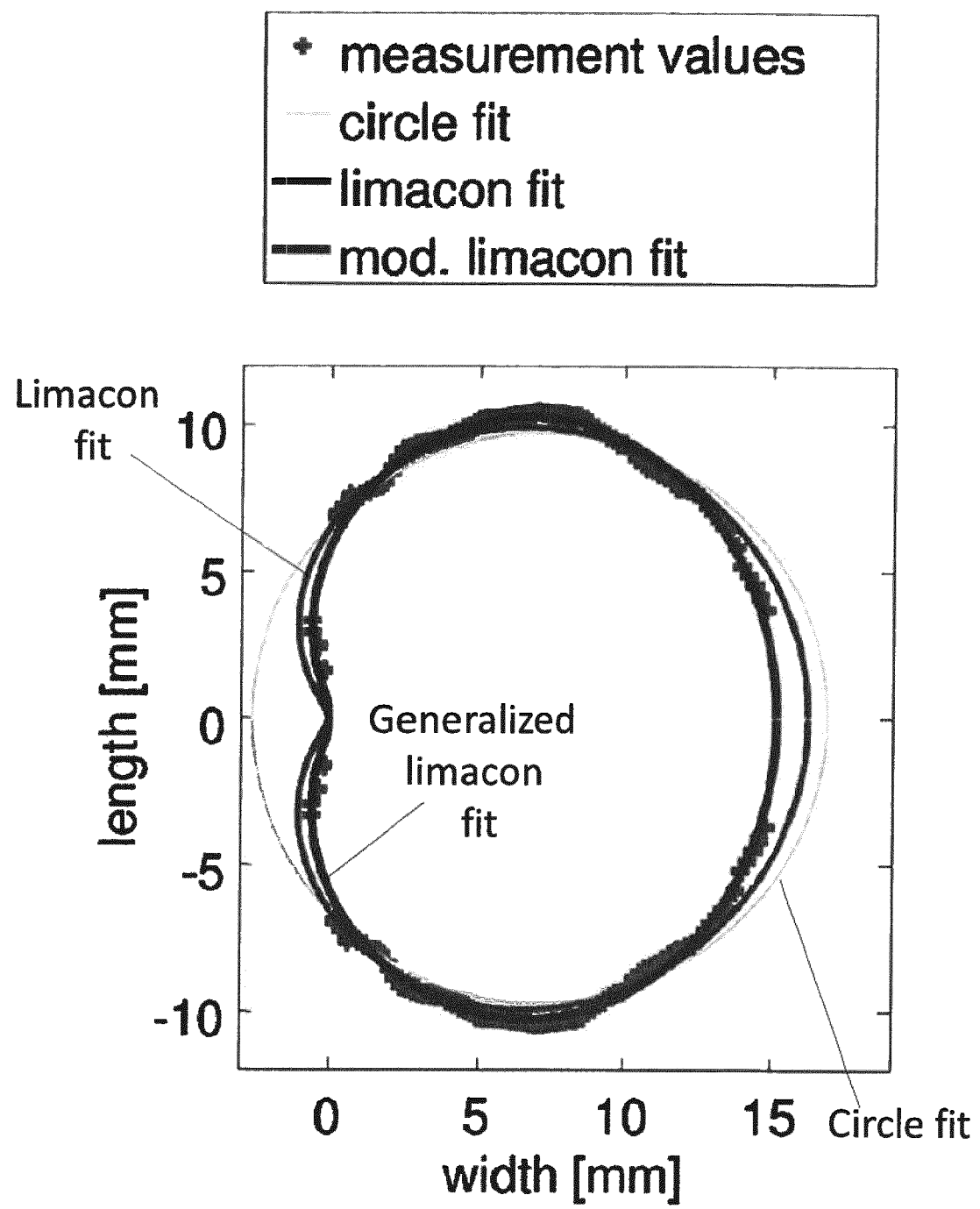

FIG. 2d shows different models for the shape of the vitreous body overlapped with the eye measurement data. In particular, there are three fits shown: a circle fit, a conventional limacon fit and a generalized limacon fit according to the geometry equation above. It can be seen that the generalized limacon fit can best describe the actual shape of the vitreous body as measured.

Further to the geometry equation, the provided model for the human eye comprises a set of equations defining a drug convection in the vitreous body. In particular, the set of equations is given by the following system:

$$\partial_t C(t, \vec{x}) + [\vec{v}(t, \vec{x}) \cdot \nabla] C(t, \vec{x}) - \nabla \cdot [D(\vec{x}) \nabla C(t, \vec{x})] = f_g$$

$$\nabla \cdot \vec{v}(t, \vec{x}) = 0,$$

$$\frac{v}{K}\vec{v}(t, \vec{x}) + \nabla p(t, \vec{x}) = h_g.$$

wherein $C(t, \vec{x})$ is the concentration of the drug, $\vec{v}(t, \vec{x})$ is the velocity of the vitreous humor, $D(\vec{x})$ is the diffusion coefficient, $f_g$ is the effect of the gravitational force on the drug concentration $C(t, \vec{x})$, $p(t, \vec{x})$ is the pressure of the vitreous humor flow, $h_g$ is the effect of the gravitational force on the vitreous humor flow, $v$ is the viscosity and $K$ is the permeability of the vitreous body.

The system of equations describes the drug convection taking into account the consistency of the vitreous body. The distribution of the drug in the vitreous body resulting from the set of equations is shown in FIG. 3d.

Figure 3A:
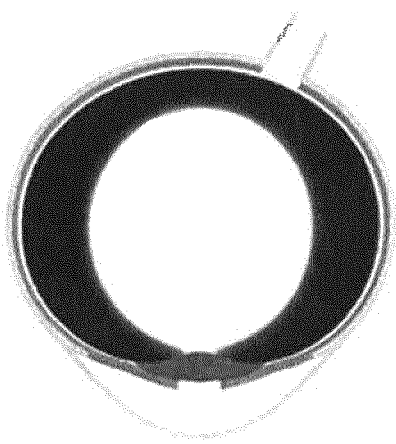
FIGS. 3a to 3d show the convection of a drug in the vitreous body under different assumptions.
Figure 3B:
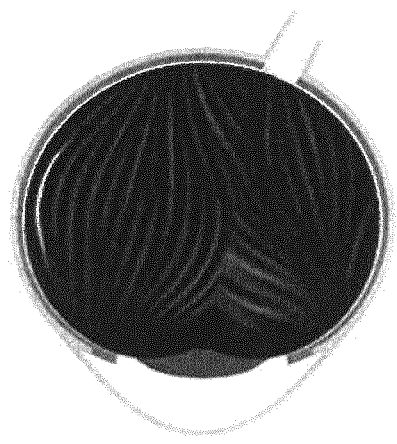
Figure 3C:
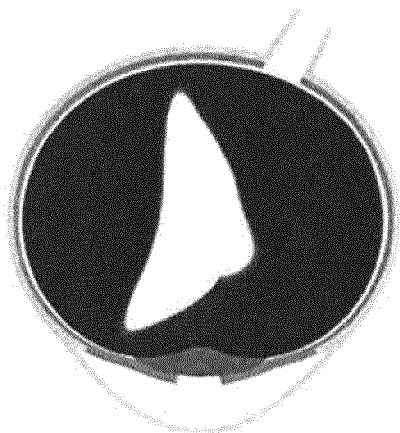
Figure 3D:
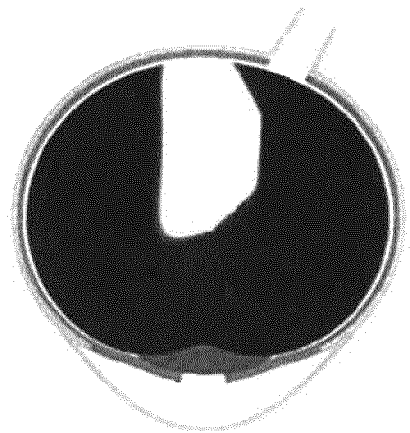

A simplified model of the drug flow in the vitreous body is shown in FIG. 3a, for which only an isotropic diffusion is assumed. However, as shown in FIG. 3b, the vitreous body contains collagen fibers creating a meshwork with a heterogeneous structure that determines an anisotropic diffusion. The result of an anisotropic ansatz is shown in FIG. 3c. However, the flow of the drug is not only due to diffusion but also to advection, since the vitreous body is made up of water up to 98%. The advection is affected by gravity and FIG. 3d shows the drug distribution once the gravity effect is also taken into account.

The diffusion coefficient for anisotropic diffusion can be described by a 3×3 matrix given by:

$$D := d_1 I + d_2 (f \otimes f), f = (\cos\theta, \sin\theta, 0)^T$$

wherein $d_1$ is a parameter describing the proportion of isotropic diffusion and $d_2$ is a parameter describing the proportion of directed diffusion along the collagen fibers. On the basis of in vivo or in vitro experiments, $d_1$ and $d_2$ are for example determined to be $d_1 = 0.3$, $d_2 = 0.7$.

Further to the three equations above, the following boundary conditions apply:

$$C(t, \vec{x}) = 0 \text{ on } \Gamma_c$$

$$p(t, \vec{x}) = 2000 \text{ Pa on } \Gamma_c$$

$$\partial_{\vec{n}} C(t, \vec{x}) = 0 \text{ on } \Gamma_l$$

$$\vec{v}(t, \vec{x}) = 0 \text{ on } \Gamma_l$$

$$-D(\vec{x})\partial_{\vec{n}} C(t, \vec{x}) - PC(t, \vec{x}) + [\vec{n}(\vec{x}) \cdot \vec{v}(t, \vec{x})](1 - k)C(t, \vec{x}) = 0 \text{ on } \Gamma_r$$

$$[\vec{n}(\vec{x}) \cdot \vec{v}(t, \vec{x})] = K_R \frac{p(t, \vec{x}) - P_v}{L} \text{ on } \Gamma_r$$

wherein $\Gamma_c$ is the boundary towards the ciliary body, $\Gamma_l$ towards the lens and $\Gamma_r$ towards the retina. $P = 2.6 \cdot 10^{-7}$ m/s is the retinal permeability, $n$ is the unit normal vector to the surface of the vitreous body, k=7.9 is the partition coefficient between the vitreous body and the retina, $K_R$ is the hydraulic conductivity of the retina, choroid and sclera, equal to $1.5 \cdot 10^{-15}$ m²/(Pa s), $P_v$=1200 Pa is the pressure of the episcleral tissue and L=$3 \cdot 10^{-4}$ m is the thickness of retina, choroid and sclera. The term $\partial_{\vec{n}} C(t, \vec{x})$ is defined as $\nabla C(t, \vec{x}) \cdot \vec{n}(\vec{x})$.

The boundary conditions are determined by the outflow mechanisms and depend on the physical process by which the drug is absorbed into the parts of the eye surrounding the vitreous body bulk. The vitreous humor can leave via the retina according to a certain permeability and the drug can leave as well with a different permeability.

The method further comprises setting a target drug state in the vitreous body at step 130. This is done by setting constraints for one or both of the following performance factors:

$$J_1(t) := \frac{\int_\Omega C(t, \vec{x}) dx}{\int_\Omega C(0, \vec{x}) dx}$$

i.e. the relative amount of drug left in the whole volume $\Omega$ of vitreous body at a given time with respect to the initial amount, and $$J_2(t) := \int_{B_r} C(t, \vec{x}) dx$$

i.e. the amount of drug in a specific region $B_r$ around the macula. The region $B_r$ around the macula may be defined by a sphere with center with e.g. coordinates (14 mm, 0, 0) and radius of about 2 mm.

For example, the target drug state can correspond to the satisfaction of the following conditions: $J_1(\bar{t}_1) \geq 0.2$ and $J_1(\bar{t}_2) \geq 0.05$, wherein $\bar{t}_1$ is 48 hours and $\bar{t}_2$ is 96 hours. Such a target drug state can be set for drugs that have a long-lasting effect and that must act for prolonged time periods, such as Aflibercept. In another example, the target drug state can be set by setting the following condition: $J_2(\bar{t}_3) \geq 0.6$, with $\bar{t}_3$ being 24 hours. This is the case when an intensified treatment is required, e.g. for a thick edema.

Figure 4B:
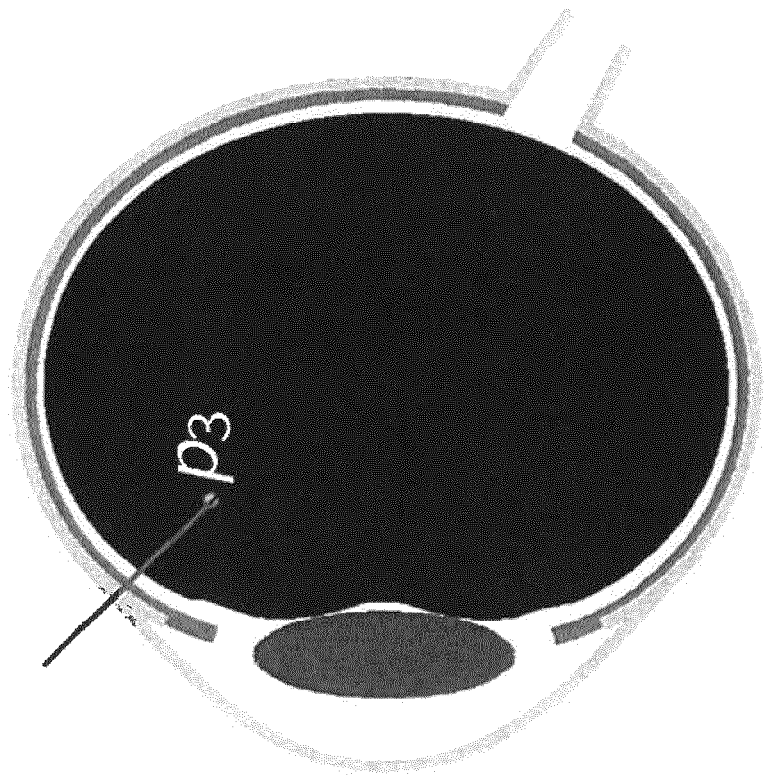
FIGS. 4a and 4b show exemplary injection points for the ocular drug delivery.
Figure 4A:
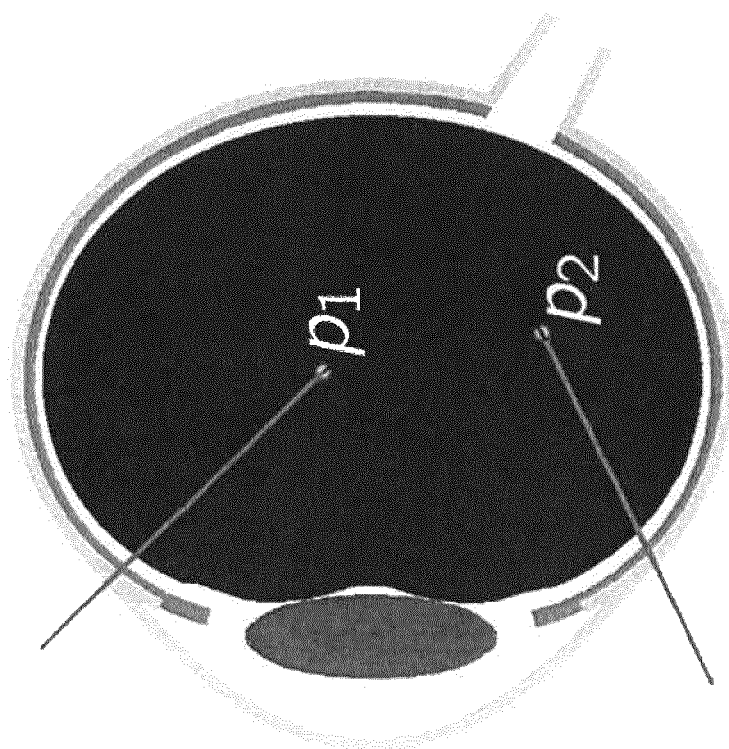

The method further comprises performing at least one simulation to obtain a simulated drug state at step 150. In particular, a plurality of simulations are performed, each for a different injection point. The injection position is one of the initial conditions for the simulation. For example, the three injection positions shown in FIGS. 4a and 4b can be tested. FIG. 4a shows a first injection position $P_1$ at 10 mm from limbus via pars plana, direction towards the center of the posterior pole and a second injection position $P_2$ at 8 mm from limbus via pars plana, direction sideward towards the posterior pole. FIG. 4b shows a third injection position $P_3$ at 3 mm from limbus via pars plana, direction towards the center of the posterior pole.

The simulation is performed by numerically solving the flow equations and the boundary conditions and the concentration function $C(t, \vec{x})$ defining the drug state is obtained as a result. Based on the concentration function, the values for the performance factors at different time points may be calculated.

Figure 5:
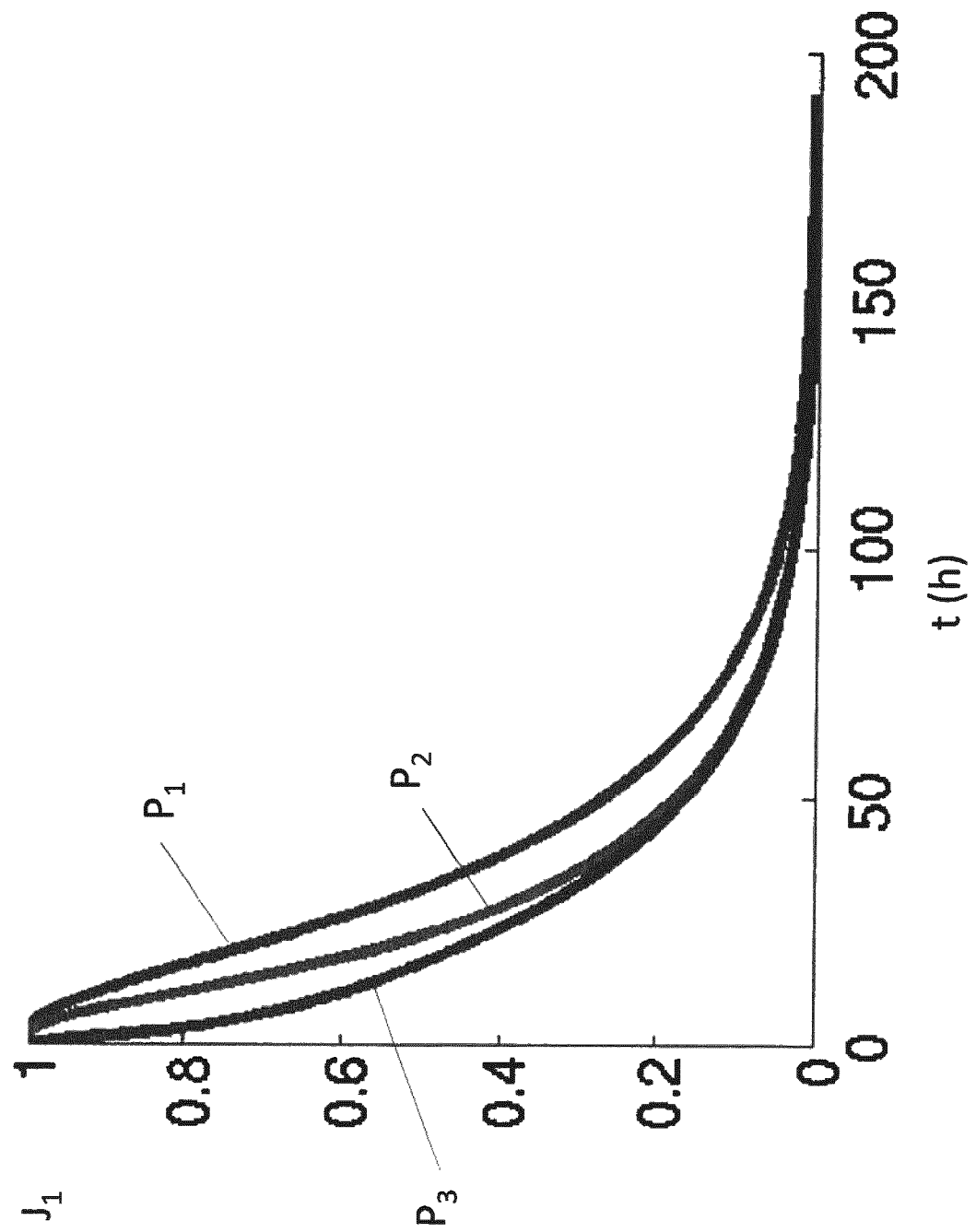
FIG. 5 shows how the relative amount of drug in the vitreous body with respect to the initial amount changes with time for different injection positions.
Figure 6:
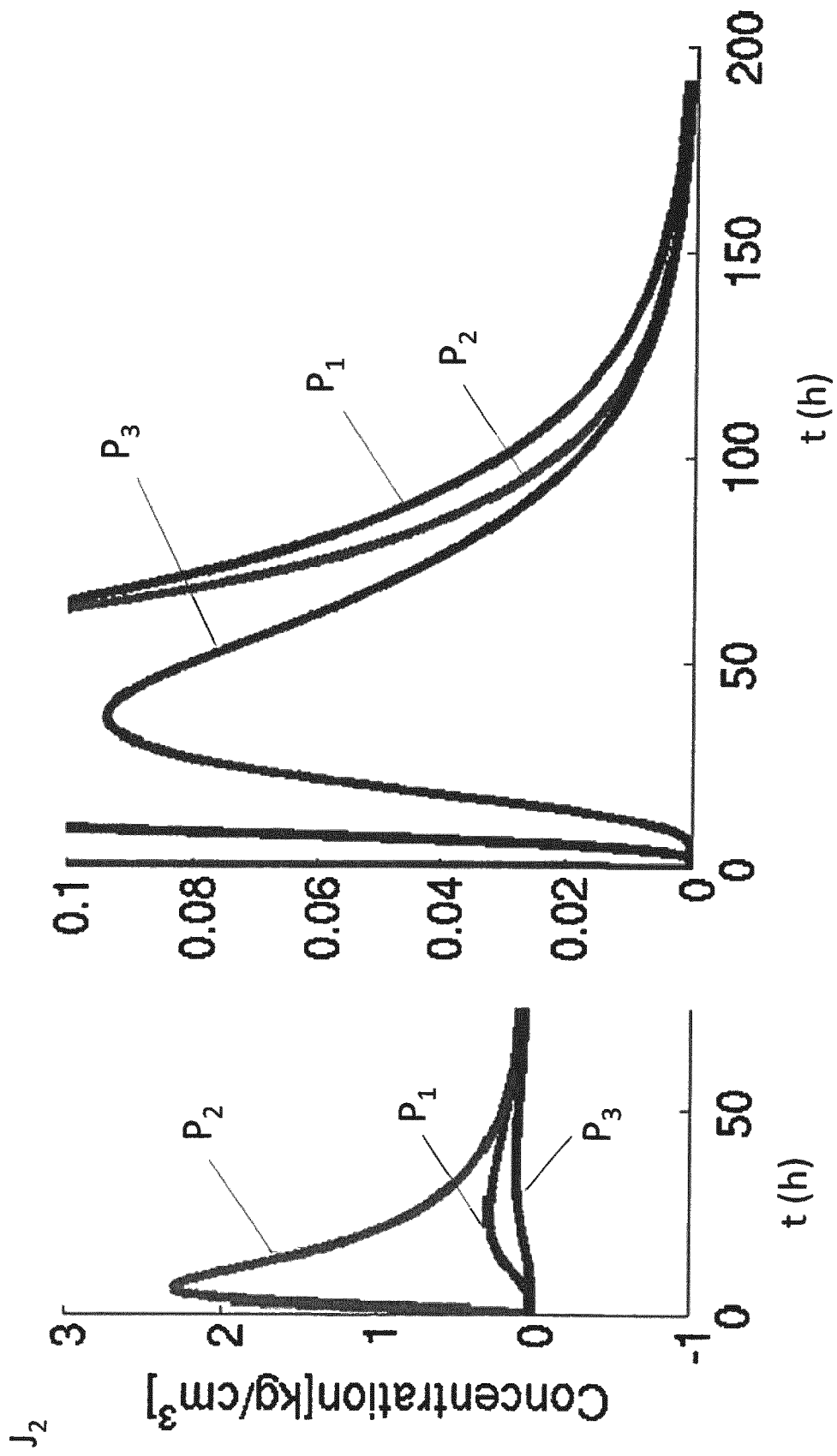
FIG. 6 shows how the amount of drug in a region close to the macula changes with time for different injection positions.

FIG. 5 shows $J_1(t)$ as a function of time (expressed in hours) for the three different simulations corresponding to the three injections points shown in FIG. 4. FIG. 6 shows $J_2(t)$ as a function of time (expressed in hours) for the three different simulations corresponding to the three injections points shown in FIG. 4. It can be seen that, when injected at position $P_1$, the drug remains longest in the vitreous body, while an injection at position $P_2$ leads to the highest value of the amount of the drug around the macula in the first two days.

The following tables report the simulated values for $J_1(t)$ and $J_2(t)$ at 24, 48, 96 and 192 hours after injection:

TABLE 1

| Time t [hours] | $J_1$ for $P_1$ | $J_1$ for $P_2$ | $J_1$ for $P_3$ |
| --- | --- | --- | --- |
| 24 | 0.63 | 0.46 | 0.39 |
| 48 | 0.28 | 0.18 | 0.17 |
| 96 | 0.053 | 0.034 | 0.032 |
| 192 | 0.0018 | 0.0011 | 0.0011 |

TABLE 2

| Time t [hours] | $J_2$ for $P_1$ | $J_2$ for $P_2$ | $J_2$ for $P_3$ |
| --- | --- | --- | --- |
| 24 | 0.26 | 0.79 | 0.069 |
| 48 | 0.16 | 0.2 | 0.082 |
| 96 | 0.035 | 0.025 | 0.02 |
| 192 | 0.0012 | 0.0008 | 0.00076 |

The method comprises comparing the target drug state and the simulated drug states at step 170. In particular, the method comprises computing a plurality of deviation scores for the plurality of simulations based on the comparison between the target drug state and the plurality of simulated drug states and selecting an optimal injection position based on the deviation scores.

For the above example in which the target drug state was set as: $J_2(\bar{t}_3) \geq 0.6$, with $\bar{t}_3$ being 24 hours, the following deviation scores are computed as differences between the simulated values and the lower limit 0.6: $-0.34$ for $P_1$, 0.19 for $P_2$, and $-0.531$ for $P_3$. In another example, the deviation score may be defined such that all negative values are brought to zero, e.g. as a step function of the difference. This could make the evaluation of the comparison easier, in that the optimal injection position can be determined simply by looking for the highest deviation score.

Accordingly, of the three injection positions tested, $P_2$ is the most suitable for intensive treatment of the area around the macula. The simulation allows to accurately assess the efficacy of the different injection positions without the need to experiment on a patient.

Other medical treatments besides the ocular drug delivery can be tested and optimized following the principles of the illustrated method. In some cases, it may be necessary to provide modelling for other components of the eye besides the vitreous body. In the following, mathematical equations realistically describing the geometry of various components are presented:

Natural Lens

The ocular lens is given by a combination of two semi-ellipsoids, one for the front part of the lens:

$$\frac{(x-3.8)^2}{a^2} + \frac{y^2}{b^2} + \frac{z^2}{c^2} \leq 1, \forall x, y, z \in \mathbb{R} \text{ and } x \geq 3.8$$

with a=5 mm, b=5 mm and c=1.5 mm, and one for the rear part of the lens $$\frac{(x-3.8)^2}{a^2} + \frac{y^2}{b^2} + \frac{z^2}{c^2} \le 1, \forall\, x, y, z \in \mathbb{R} \text{ and } x \le 3.8$$

with a=5 mm, b=5 mm and c=2.5 mm. The values for the parameters refer to an average human eye. The diameter of the lens varies between 6.5 and 9 mm. The thickness of the lens varies between 3.5 and 5 mm.

Figure 7:
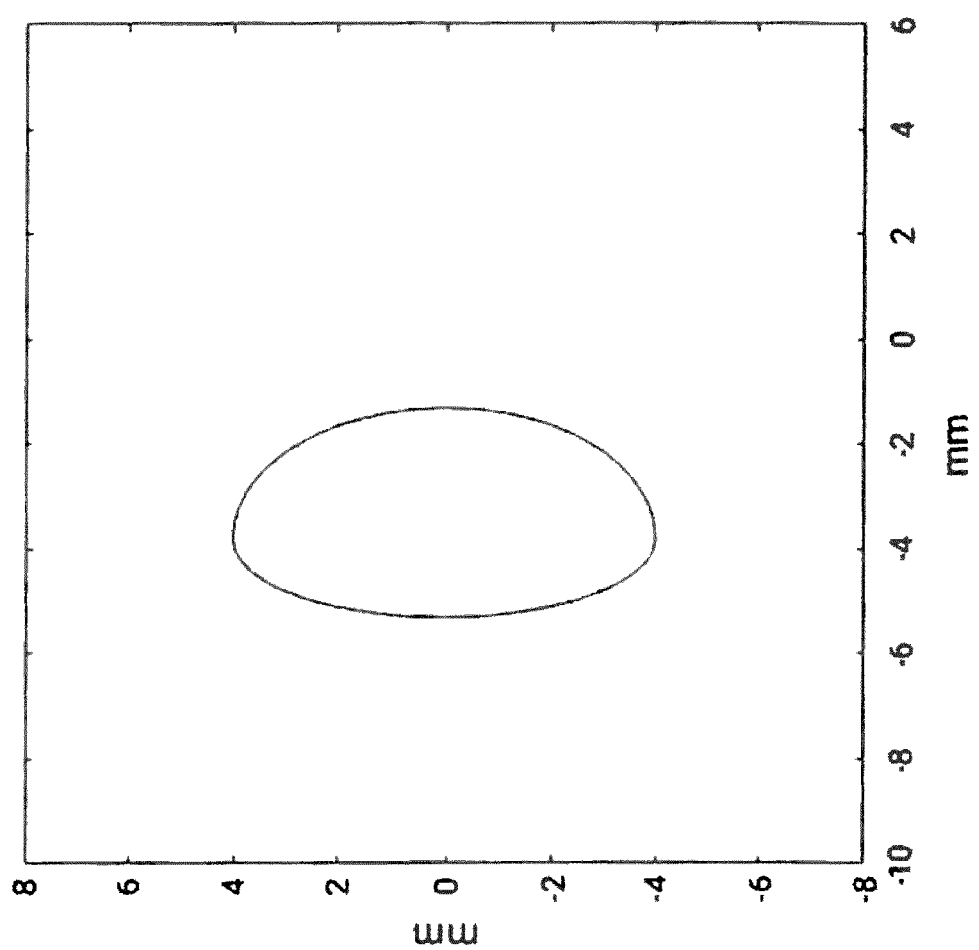
FIG. 7 shows a geometric model for the shape of the lens.

A two-dimensional projection of the three-dimensional model for the natural lens is shown in FIG. 7.

Artificial Lens

An artificial lens configured to replace a natural lens is modelled as a very thin cylinder with two branches. The cylinder has a thickness $h_{lens}$ of about 1 mm and a diameter $R_{lens}$ between about 5 mm and about 7 mm:

$$z^2+y^2=R_{lens}^2, x\in[3.8, h_{lens}+3.8]$$

The branches are given by $$SG_3:=\{y,z\in DZ | z\in[0,-3], y\in[4,6]\}$$

$$SG_4:=\{y,z\in DZ | z\in[0,3], y\in[-6,-4]\}$$

with $DZ:=EG/EG_1$ and $$EG := \left\{z, y \in \mathbb{R} \;\Big|\; \frac{z^2}{\left(\frac{9}{\sqrt{5}}\right)^2} + \frac{y^2}{6^2} \le 1\right\},$$

$$EG_1 := \left\{z, y \in \mathbb{R} \;\Big|\; \frac{z^2}{a_3^2} + \frac{y^2}{b_3^2} \le 1\right\}$$

with $a_3=5.5$ mm and $b_3=3.92939$ mm and $x\in[3.8, 4.2]$.

Figure 8:
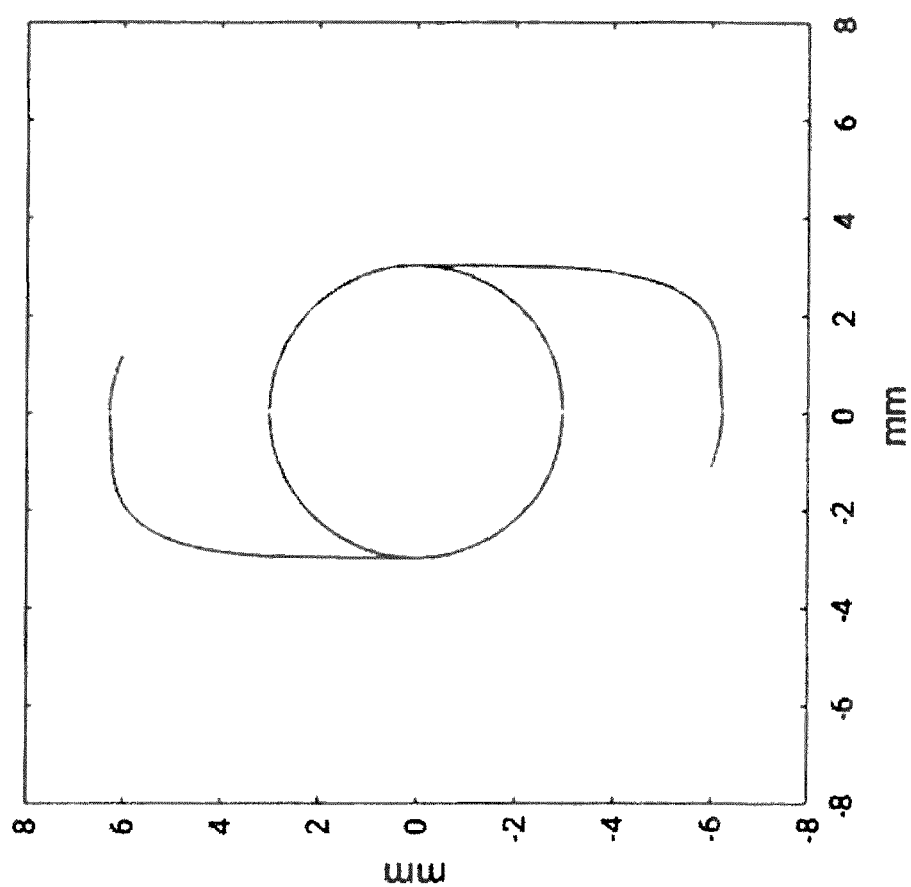
FIG. 8 shows a geometric model for the shape of an artificial lens.

A two-dimensional projection of the three-dimensional model for the artificial lens is shown in FIG. 8.

Healthy Iris

The healthy iris is represented by the following set of points belonging to the healthy eye (HE):

$$I:=\{x,y,z\in HE | z^2+y^2>R^2, x\in[a,b]\}$$

R is the radius of the pupil, a=5.6 mm is the iris bottom boundary and b=6.0 mm is the upper iris boundary. The distance between the lens and the iris is 0.4 mm and the thickness of the iris is 0.5 mm. By daylight, the radius of the pupil R is about 1-2 mm and at night the pupil can reach a radius of about 9 mm. R can be set to any number in this range.

Figure 9B:
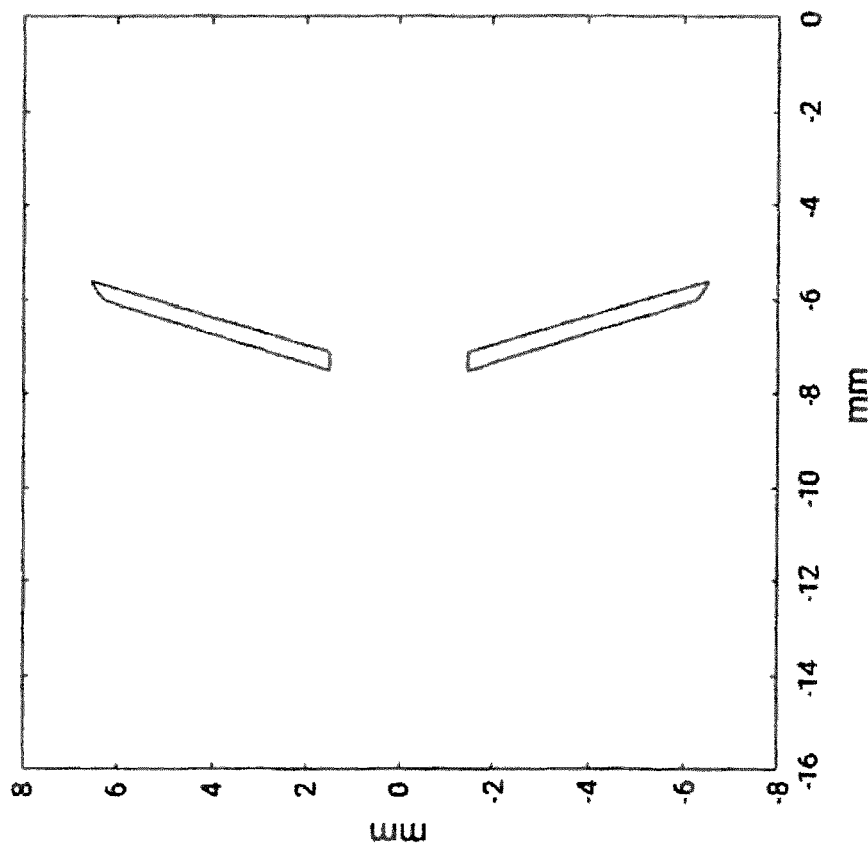
FIG. 9b shows a geometric model for the shape of a pathological iris.
Figure 9A:
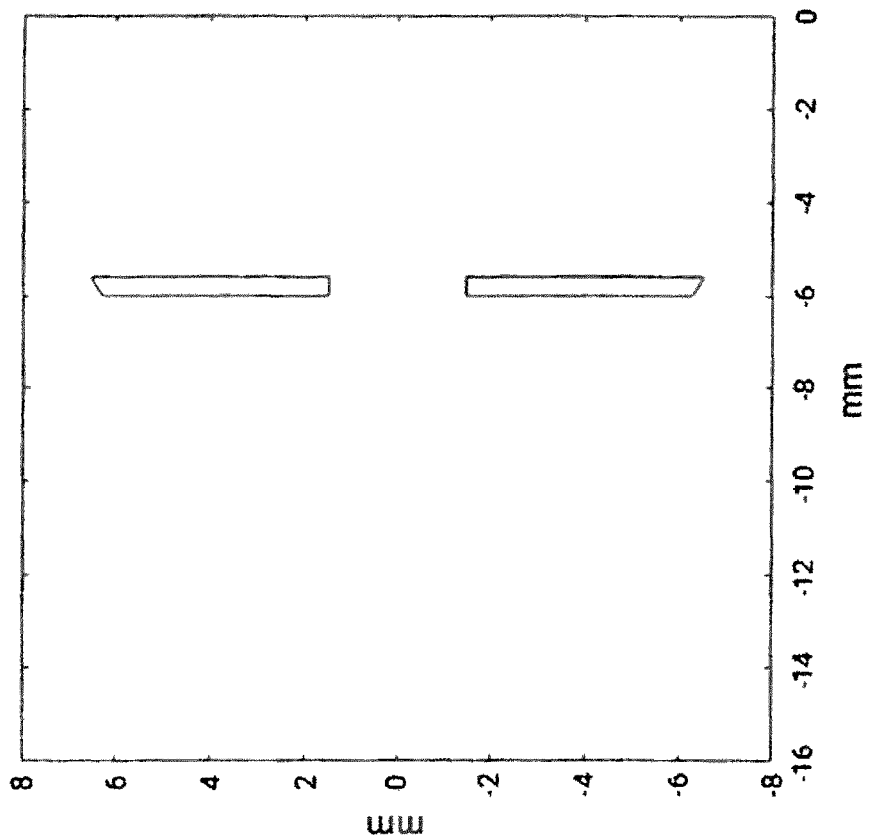
FIG. 9a shows a geometric model for the shape of a healthy iris.

A two-dimensional projection of the three-dimensional model for the healthy iris is shown in FIG. 9a.

Pathological Iris

The pathological iris is modelled as a section of a truncated cone with a hole. The mathematical description is built as follows:

a truncated cone with the height h of 1.5 mm, the small radius of 3 mm and the big radius of 7 mm is defined as $$M_1:=\{x,y,z\in \mathbb{R} | z^2+y^2=R_{ks}^2(x-H-s)^2, \forall x\in[s,h+s]\}$$

a truncated cone with the height h of 1 mm, the small radius of 3 mm and the big radius of 7 mm is defined as $$M_2:=\{x,y,z\in \mathbb{R} | z^2+y^2=R_{ks}^2(x-H-s+a)^2, \forall x\in[s,h-a+s]\}$$

the second cone is subtracted from the first cone to obtain $M:=M_1/M_2$ a cylinder with a radius of 3 mm and a height of 0.5 mm is subtracted from the geometrical object M to obtain the iris $$I:=M\setminus\{x,y,z\in \mathbb{R} | z^2+y^2=R_z^2, x\in[h+3.4, h+3.8]\}$$

In the above equations, H is the height of the cone $$H = h\frac{r_{AC}}{r_{ac}-r_p}$$

where $r_{ac}$ is the half of the anterior chamber width $r_{AC}$, with $r_{AC}=7$ mm, generally in a range between 5.9 mm and 7.2 mm, and $r_p=1.5$ mm, generally in a range between 1 mm and 5 mm, is the radius of the pupil. $R_{ks}$ is the radius of the circle at the origin in the (y,z) plane and is equal to $r_{AC}/h$, s=3.8 mm is the shift in the x coordinate, a is the thickness of the iris, which is in the range between 0.3 mm and 0.6 mm, e.g. 0.4 mm, and $R_z$ is the radius of the pupil in the range between 1.5 mm and 6 mm, e.g. 3 mm.

A two-dimensional projection of the three-dimensional model for the pathological iris is shown in FIG. 9b.

Ciliary Body

The function cb(x) describing the inner boundary of the ciliary body is given by:

$$cb(x) = \begin{cases} a_1(x+4.5)^2 + a_2 & \text{for } -5.5 \le x \le -4.6 \\ a_3(x+3.5)^2 + a_4 & \text{for } -4.61 \le x \le -1.7 \\ a_5 \exp x + a_6 & \text{for } -1.7 \le x \le 3.66 \end{cases}$$

with $a_1=1.527403$, $a_2=-6.298481581$, $a_3=0.7956$, $a_4=5.2997$, $a_5=1.3501$ and $a_6=7.1379$. The three-dimensional surface is given by the set of points
$[x, cb(x) \cos(\phi), cb(x) \sin(\phi)]$
with $x\in[-5.5; 3.66]$ and $\phi\in[0, 2\pi)$.

Figure 10:
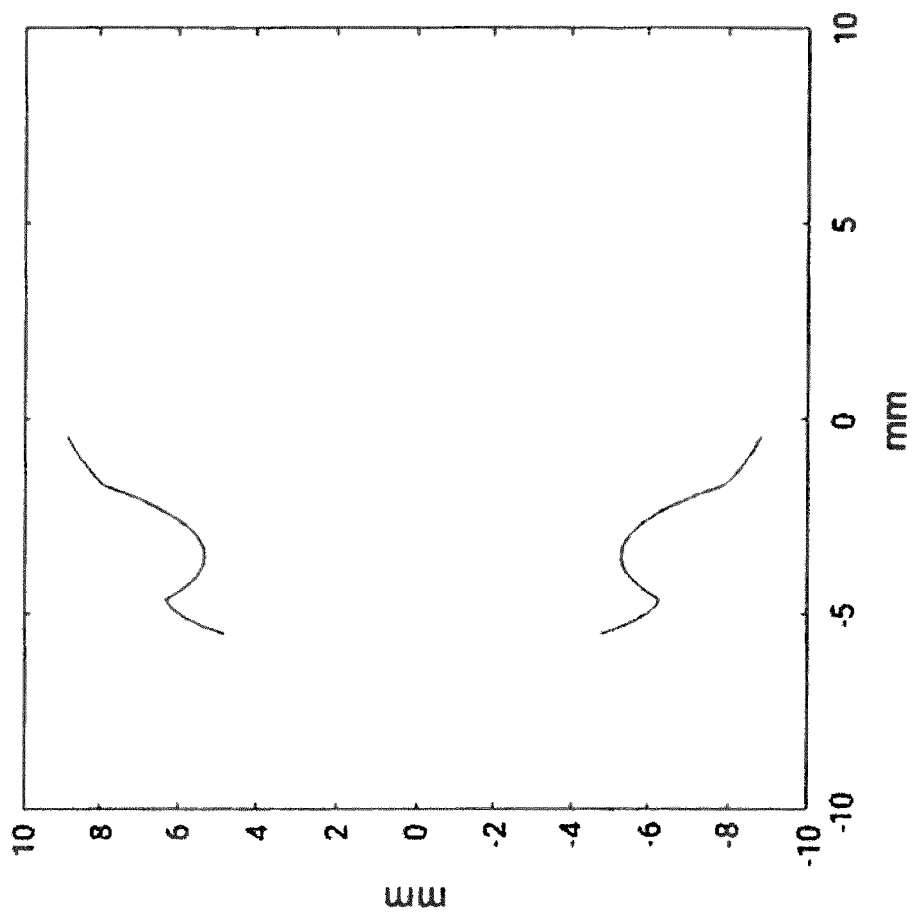
FIG. 10 shows a geometric model for the shape of the ciliary body.

A two-dimensional projection of the three-dimensional model for the ciliary body is shown in FIG. 10.

Sclera and Cornea

The covering of the human eye consists of the sclera and cornea and is given by following function:

$$eye(x) = \begin{cases} \sqrt{bb^2 - \left(\frac{(x-4.2)\cdot bb}{aa}\right)^2} & \text{for } 8 \le x \le 15 \\ c_1(x-5.2)^2 + c_2 & \text{for } -3 \le x \le 8 \\ c_3 \exp x + c_4 & \text{for } -5 \le x \le -3 \\ \sqrt{b^2 - \left(\frac{(x-4.2)\cdot b}{a}\right)^2} & \text{for } -8.8 \le x < -5 \end{cases}$$

with bb=11.6, aa=10.8, a=5, b=7.1, $c_1=-0.0413$, $c_2=11.1802$, $c_3=35.0925$, and $c_4=6.6560$. The three-dimensional surface is given by the set of points $[x, eye(x) \cos(\phi), eye(x) \sin(\phi)]$
with $x\in[-8.8; 15]$ and $\phi\in[0, 2\pi)$.

Figure 11:
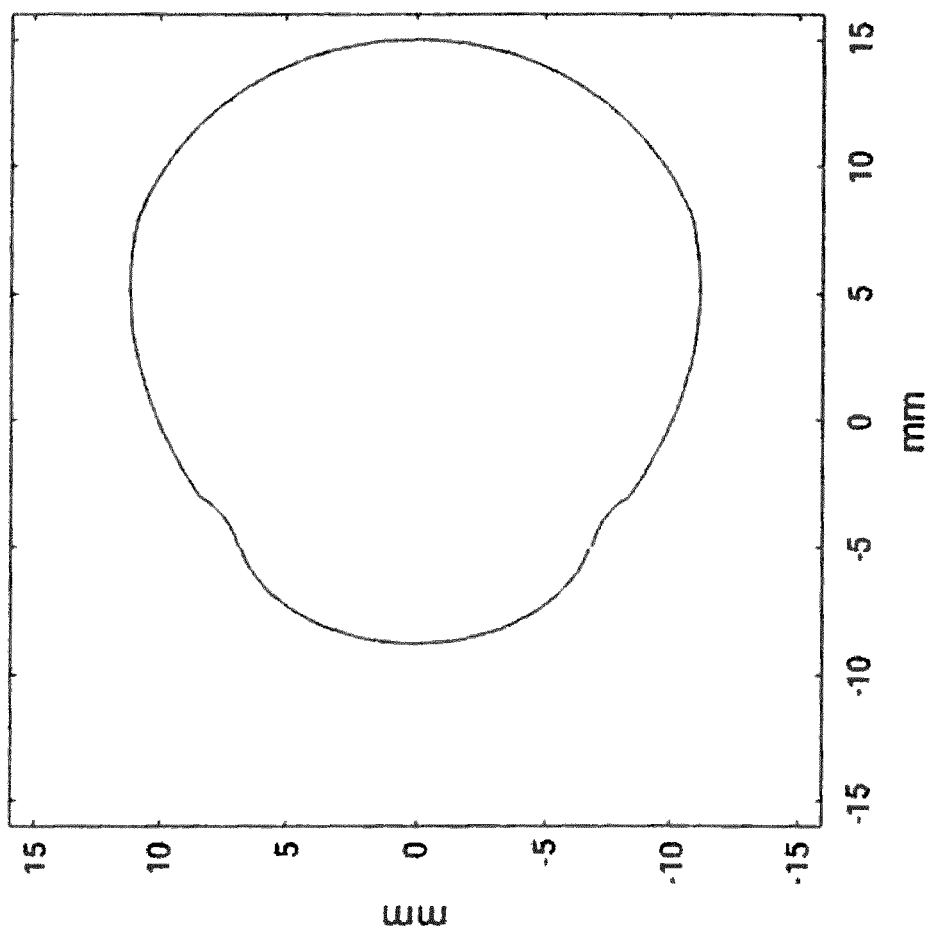
FIG. 11 shows a geometric model for the shapes of the sclera and cornea.

A two-dimensional projection of the three-dimensional model for the sclera and cornea is shown in FIG. 11.

Anterior Chamber

The geometrical form of the anterior chamber is assumed to be a semi-ellipsoid with the principal axes of the length a=5, b=7, c=7. The mathematical equation is given by $$\frac{(x-3.8)^2}{a^2} + \frac{y^2}{b^2} + \frac{z^2}{c^2} \leq 1, \forall\, x, y, z \in \mathbb{R} \text{ and } x \geq 3.8$$

Furthermore, the iris and the ciliary body are inside of the anterior chamber and must be removed from the semi-ellipsoid, no longer belonging to the anterior chamber.

Figure 12:
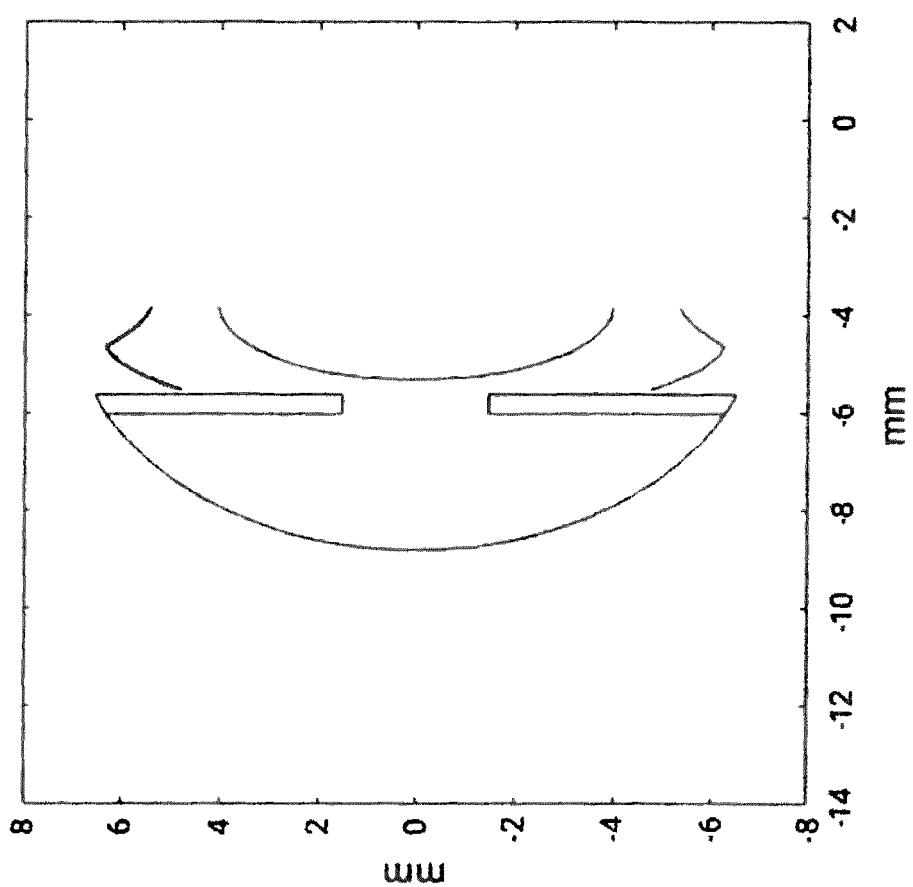
FIG. 12 shows a geometric model for the shape of the anterior chamber.

A two-dimensional projection of the three-dimensional model for the anterior chamber is shown in FIG. 12.

A combination of all components is shown in FIG. 13, which represents a model for the whole eye that can be used for numerical simulations of physiological processes and therapeutic approaches.

The invention claimed is:

1. A computer-implemented method for testing and optimizing ocular drug delivery, wherein the ocular drug delivery is characterized by a set of delivery parameters comprising at least one of drug type, drug concentration, drug amount, injection position, or penetration depth, the method comprising:
   employing an ultrasound imaging technique or an optical coherence tomography technique to gather eye measurement data;
   obtaining a model for a human eye via the eye measurement data, wherein the model comprises:
      a geometry equation defining a three-dimensional limacon for geometry of a vitreous body of the model for the human eye, wherein the geometry equation is $x = R(\varphi)\cos\varphi + m_x$ $y = R(\varphi)\sin\varphi \cos\theta$ $z = R(\varphi)\sin\varphi \sin\theta$ with $R(\varphi) = (p_1 + p_2\cos\varphi + p_3\cos\varphi^3)$, $\theta \in [0, \pi)$, $\varphi \in [0, 2\pi)$; and
      a set of equations defining a drug convection in the vitreous body of the model for the human eye;
   setting a target drug state in the vitreous body of the model for the human eye;
   using the model to perform at least one simulation of the ocular drug delivery with a given set of values for the set of delivery parameters, wherein the at least one simulation provides a simulated drug state in the vitreous body of the model for the human eye; and
   comparing the target drug state and the simulated drug state.

2. The computer-implemented method according to claim 1, wherein the geometry equation is a parameterized geometry equation including a set of free geometry parameters, the method further comprising:
   retrieving eye measurement data describing at least a shape of the vitreous body of the model for the human eye; and
   determining a set of values for the set of free geometry parameters by fitting the parameterized geometry equation to the eye measurement data.

3. The computer-implemented method according to claim 2, wherein retrieving eye measurement data further comprises collecting the eye measurement data.

4. The computer-implemented method according to claim 1, further comprising defining a performance factor characterizing a drug state, wherein:
   setting the target drug state comprises setting a target constraint for the performance factor;
   providing a simulated drug state comprises computing a simulated value for the performance factor;
   comparing the target drug state and the simulated drug state comprises comparing the simulated value with the target constraint.

5. The computer-implemented method according to claim 1, wherein:
   the model is used to perform a plurality of simulations of the ocular drug delivery, each simulation being performed with a different set of values for the set of delivery parameters and each simulation providing a simulated drug state of a plurality of simulated drug states in the vitreous body of the model for the human eye;
   the method further comprising:
      computing a plurality of deviation scores for the plurality of simulations based on comparing the target drug state and the plurality of simulated drug states; and
      selecting an optimal set of values for the set of delivery parameters based on the deviation scores.

6. The computer-implemented method according to claim 1,
   wherein the method further comprises:
      generating a visual representation of the simulated drug state in the vitreous body of the model for the human eye; and
      outputting the visual representation via an output device;
   and/or
      wherein the model for the human eye further comprises a plurality of geometry equations defining geometry of all components of the human eye and the method further comprises:
         three-dimensionally printing the model for the human eye using the plurality of geometry equations.

7. The computer-implemented method according to claim 1, wherein $p_1 \in [7.5, 7.7]$ and/or $p_2 \in [9.0, 9.2]$ and/or $p_3 \in [-2.5, -2.8]$ and/or $m_x \in [-1, -1.2]$.

8. The computer-implemented method according to claim 1, further including performing a plurality of simulations for a plurality of injection points, wherein each injection point is located at a different injection position in the vitreous body of the model for the human eye.

9. A computer system for testing and optimizing ocular drug delivery, wherein the ocular drug delivery is characterized by a set of delivery parameters comprising at least one of drug type, drug concentration, drug amount, injection position, penetration depth, the computer system comprising:
   a storage unit configured to provide or receive eye measurement data gathered via ultrasound imaging techniques or optical coherence tomography techniques and further used to generate a model for a human eye, wherein the model comprises:
      a geometry equation defining a three-dimensional limacon for geometry of a vitreous body of the model for the human eye, wherein the geometry equation is $x = R(\varphi)\cos\varphi + m_x$ $y = R(\varphi)\sin\varphi \cos\theta$ $z = R(\varphi)\sin\varphi \sin\theta$ with $R(\varphi) = (p_1 + p_2\cos\varphi\, p_3\cos\varphi^3)$, $\theta \in [0, \pi)$, $\varphi \in [0, 2\pi)$; and
      a set of equations defining a drug convection in the vitreous body of the model for the human eye;

a processing and control unit configured to perform the following:
setting a target drug state in the vitreous body of the model for the human eye;
using the model to perform at least one simulation of the ocular drug delivery with a given set of values for the set of delivery parameters, wherein the at least one simulation provides a simulated drug state in the vitreous body of the model for the human eye; and
comparing the target drug state and the simulated drug state.

10. The computer system according to claim 9, wherein the geometry equation is a parameterized geometry equation including a set of free geometry parameters, the system further configured to perform the following:
retrieving eye measurement data describing at least a shape of the vitreous body of the model for the human eye; and
determining a set of values for the set of free geometry parameters by fitting the parameterized geometry equation to the eye measurement data.

11. The computer system according to claim 10, wherein the computer system is further configured to collect the eye measurement data.

12. The computer system according to claim 9, wherein a performance factor characterizes a drug state and wherein:
setting the target drug state comprises setting a target constraint for the performance factor;
providing a simulated drug state comprises computing a simulated value for the performance factor;
comparing the target drug state and the simulated drug state comprises comparing the simulated value with the target constraint.

13. The computer system according to claim 9, wherein:
the processing and control unit is configured to use the model to perform at least one simulation by performing a plurality of simulations of the ocular drug delivery, each simulation being performed with a different set of values for the set of delivery parameters and each simulation providing a simulated drug state of a plurality of simulated drug states in the vitreous body of the model for the human eye;
the processing and control unit is further configured to perform the following:
computing a plurality of deviation scores for the plurality of simulations based on comparing the target drug state and the plurality of simulated drug states; and
selecting an optimal set of values for the set of delivery parameters based on the plurality of deviation scores.

14. The computer system of claim 9, further comprising:
means for providing a plurality of geometry equations describing geometry of all components of the vitreous body of the model for the human eye; and
means for three-dimensionally printing the model for the human eye using the plurality of geometry equations.

15. The computer system of claim 14, wherein the means for providing the plurality of geometry equations describing geometry of all components of the vitreous body of the model for the human eye is the storage unit, and wherein the means for three-dimensionally printing the model for the human eye is a three-dimensional printer.

16. The computer system according to claim 9, wherein $p_1 \in [7.5, 7.7]$ and/or $p_2 \in [9.0, 9.2]$ and/or $p_3 \in [-2.5, -2.8]$ and/or $m_x \in [-1, -1.2]$.

17. The computer system of claim 9, wherein a plurality of simulations are performed for a plurality of injection points, and wherein each injection point is located at a different injection position in the vitreous body of the model for the human eye.

18. A computer-implemented method for testing and optimizing ocular drug delivery, wherein the ocular drug delivery is characterized by a set of delivery parameters comprising at least one of drug type, drug concentration, drug amount, injection position, or penetration depth, the method comprising:
employing an ultrasound imaging technique or an optical coherence tomography technique to gather eye measurement data;
obtaining a model for a human eye via the eye measurement data, wherein the model comprises:
a geometry equation defining a three-dimensional limacon for geometry of a vitreous body of the model for the human eye; and
a set of equations defining a drug convection in the vitreous body of the model for the human eye;
setting a target drug state in the vitreous body of the model for the human eye;
using the model to perform at least one simulation of the ocular drug delivery with a given set of values for the set of delivery parameters, wherein the at least one simulation provides a simulated drug state in the vitreous body of the model for the human eye;
comparing the target drug state and the simulated drug state;
generating a visual representation of the simulated drug state in the vitreous body of the model for the human eye; and
outputting the visual representation via an output device; and/or
wherein the model for the human eye further comprises a plurality of geometry equations defining geometry of all components of the human eye and the method further comprises:
three-dimensionally printing the model for the human eye using the plurality of geometry equations.

19. A computer system for testing and optimizing ocular drug delivery, wherein the ocular drug delivery is characterized by a set of delivery parameters comprising at least one of drug type, drug concentration, drug amount, injection position, penetration depth, the computer system comprising:
means for providing a plurality of geometry equations describing geometry of all components of a vitreous body of a model for a human eye;
means for three-dimensionally printing the model for the human eye using the plurality of geometry equations; and
a storage unit configured to provide or receive eye measurement data gathered via ultrasound imaging techniques or optical coherence tomography techniques and further used to generate the model for the human eye, wherein the model comprises:
a geometry equation defining a three-dimensional limacon for geometry of the vitreous body of the model for the human eye; and
a set of equations defining a drug convection in the vitreous body of the model for the human eye;
a processing and control unit configured to perform the following:
setting a target drug state in the vitreous body of the model for the human eye;

using the model to perform at least one simulation of the ocular drug delivery with a given set of values for the set of delivery parameters, wherein the at least one simulation provides a simulated drug state in the vitreous body of the model for the human eye; and
comparing the target drug state and the simulated drug state.

\* \* \* \* \*

UNITED STATES PATENT AND TRADEMARK OFFICE
CERTIFICATE OF CORRECTION

PATENT NO. : 11,830,598 B2
APPLICATION NO. : 17/046505
DATED : November 28, 2023
INVENTOR(S) : Elfriede Friedmann et al.

It is certified that error appears in the above-identified patent and that said Letters Patent is hereby corrected as shown below:

In the Claims

Column 20, Claim 9, Lines 64-65:
"with $R(\varphi)=(p_1 + p_2\cos\varphi p_3 \cos\varphi^3)$, $\theta\epsilon[0,\pi)$, $\varphi\epsilon[0,2\pi)$; and" corrected to -- with $R(\varphi)=(p_1 + p_2\cos\varphi + p_3\cos\varphi^3)$, $\theta\epsilon[0,\pi)$, $\varphi\epsilon[0,2\pi)$; and --.

Signed and Sealed this
Ninth Day of January, 2024

Katherine Kelly Vidal
*Director of the United States Patent and Trademark Office*